United States Patent
Murakami et al.

(10) Patent No.: US 8,430,555 B2
(45) Date of Patent: Apr. 30, 2013

(54) AGITATION APPARATUS, VESSEL, AND ANALYSIS APPARATUS INCLUDING AGITATION APPARATUS

(75) Inventors: Miyuki Murakami, Hino (JP); Nobuyoshi Tsuda, Hino (JP)

(73) Assignee: Beckman Coulter, Inc., Brea, CA (US)

( * ) Notice: Subject to any disclaimer, the term of this patent is extended or adjusted under 35 U.S.C. 154(b) by 1481 days.

(21) Appl. No.: 11/663,485

(22) PCT Filed: Sep. 16, 2005

(86) PCT No.: PCT/JP2005/017194
§ 371 (c)(1),
(2), (4) Date: Apr. 9, 2007

(87) PCT Pub. No.: WO2006/033308
PCT Pub. Date: Mar. 30, 2006

(65) Prior Publication Data
US 2008/0095667 A1    Apr. 24, 2008

(30) Foreign Application Priority Data

Sep. 22, 2004 (JP) .................... 2004-275229
Sep. 15, 2005 (JP) .................... 2005-268687

(51) Int. Cl.
*B01F 11/02* (2006.01)

(52) U.S. Cl.
USPC .............. 366/144; 366/127; 366/199; 422/63; 422/128

(58) Field of Classification Search .......... 422/20, 422/128, 64, 65, 127, 63, 66; 366/127, 199, 366/114

See application file for complete search history.

(56) References Cited

U.S. PATENT DOCUMENTS

| | | | | |
|---|---|---|---|---|
| 2,775,434 A | * | 12/1956 | Probst | 366/120 |
| 3,103,310 A | * | 9/1963 | Lang | 239/4 |
| 3,198,489 A | * | 8/1965 | Finch | 366/113 |
| 3,301,535 A | * | 1/1967 | Brown | 366/113 |

(Continued)

FOREIGN PATENT DOCUMENTS

| | | |
|---|---|---|
| JP | 08-146007 | 6/1996 |
| JP | 2001-272404 | 10/2001 |

(Continued)

OTHER PUBLICATIONS

U.S. Appl. No. 60/513,857, filed Oct 24, 2003, Specification, Connelly et al. 12 pages.*

(Continued)

*Primary Examiner* — Tony G Soohoo
(74) *Attorney, Agent, or Firm* — Kilpatrick Townsend & Stockton LLP

(57) ABSTRACT

Provided are an agitation apparatus, a vessel, and an analysis apparatus including the agitation apparatus that have excellent energy transmission efficiency, and simplified structure allowing downsizing, and are easy to perform maintenance. An agitation apparatus (20), a vessel (5), and an analysis apparatus (1) including the agitation apparatus agitate a liquid retained in the vessel (5) using sound waves. The agitation apparatus (20) includes a power transmitter (21) that transmits power, an electric terminal (24c) that receives the power transmitted from the power transmitter and changes a relative arrangement with respect to the power transmitter when an arrangement of at least one of the power transmitter and the electric terminal (24c) changes, and a sound wave generator (24b) that generates sound waves by converting the power received by the electric terminal (24c) to agitate the liquid.

22 Claims, 27 Drawing Sheets

U.S. PATENT DOCUMENTS

| | | | | |
|---|---|---|---|---|
| 3,542,345 | A * | 11/1970 | Arthur | 366/113 |
| 3,596,883 | A * | 8/1971 | Brech | 366/115 |
| 3,730,489 | A * | 5/1973 | Morita | 366/113 |
| 3,932,131 | A * | 1/1976 | Rolfo-Fontana | 436/45 |
| 5,071,625 | A * | 12/1991 | Kelln et al. | 422/72 |
| 5,567,387 | A * | 10/1996 | Versluys et al. | 422/67 |
| 5,580,524 | A * | 12/1996 | Forrest et al. | 422/63 |
| 6,045,755 | A * | 4/2000 | Lebl et al. | 506/33 |
| 6,106,781 | A * | 8/2000 | Rosenberg | 422/64 |
| 6,413,783 | B1 * | 7/2002 | Wohlstadter et al. | 436/517 |
| 6,777,245 | B2 * | 8/2004 | Wixforth | 436/180 |
| 7,808,642 | B2 * | 10/2010 | Connelly et al. | 356/440 |
| 2002/0026833 | A1 * | 3/2002 | Autrey et al. | 73/643 |
| 2002/0083771 | A1 * | 7/2002 | Khuri-Yakub et al. | 73/589 |
| 2003/0008296 | A1 | 1/2003 | Hori et al. | |
| 2004/0115097 | A1 * | 6/2004 | Wixforth et al. | 422/100 |
| 2004/0257906 | A1 * | 12/2004 | Scriba et al. | 366/127 |
| 2006/0042671 | A1 * | 3/2006 | Connelly et al. | 134/184 |
| 2009/0009770 | A1 * | 1/2009 | Connelly et al. | 356/440 |

FOREIGN PATENT DOCUMENTS

| | | |
|---|---|---|
| JP | 2004-085443 | 3/2004 |
| JP | 2004/076046 | 9/2004 |
| JP | 2005-504623 | 2/2005 |
| WO | 03/018181 A1 | 3/2003 |
| WO | WO 03/ 018181 A1 * | 6/2003 |

OTHER PUBLICATIONS

U.S. Appl. No. 60/513,857, filed Oct 24, 2003, Drawings, Connelly et al., 5 drawing sheets.*

* cited by examiner

AGITATION APPARATUS, VESSEL, AND ANALYSIS APPARATUS INCLUDING AGITATION APPARATUS

TECHNICAL FIELD

The present invention relates to an agitation apparatus, a vessel, and an analysis apparatus including the agitation apparatus.

BACKGROUND ART

A conventionally known agitator that agitates a liquid using sound waves is, for example, an agitator which is employed in a chemical analysis apparatus and includes a sound wave generator arranged outside a vessel retaining a liquid and agitates the liquid by directing the sound waves generated from the sound wave generator toward the vessel (see, for example, Patent Document 1).
Patent Document 1: Japanese Patent No. 3168886

DISCLOSURE OF INVENTION

Problem to be Solved by the Invention

An agitator disclosed in Patent Document 1 includes a sound wave generator arranged outside a vessel, and a constant-temperature water is arranged between the vessel and the sound wave generator to maintain the temperature of the liquid at a constant level, whereby the vessel and the sound wave generator are distanced from each other. Therefore, when the agitator of Patent Document 1 is employed, sound waves generated from the sound wave generator are attenuated before reaching the vessel, and energy transmission efficiency is not favorable. Further, since the agitator of Patent Document 1 has a thermobath retaining the constant-temperature water, the agitator has a complicated configuration and bulky; and still further, the presence of the constant-temperature water complicates maintenance work.

In view of the foregoing, an object of the present invention is to provide an agitation apparatus, a vessel, and an analysis apparatus including the agitation apparatus, that realize excellent energy transmission efficiency, simplified configurations, downsizing, and simple maintenance work.

Means for Solving Problem

An agitation apparatus according to one aspect of the present invention agitates a liquid retained in a vessel using sound waves, and includes a power transmitter that transmits power; a power receiver which receives the power transmitted from the power transmitter and whose relative arrangement with respect to the power transmitter is changeable when an arrangement of at least one of the power transmitter and the power receiver is changed; and a sound wave generator that generates sound waves to agitate the liquid by converting the power received by the power receiver.

Further, the agitation apparatus may further include a positioner that adjusts and determines relative arrangement of the power transmitter and the power receiver.

Further, in the agitation apparatus, the positioner may adjust the relative arrangement so that a distance between the power transmitter and the power receiver is different in a power-transmission time and non-power-transmission time.

Further, in the agitation apparatus, the positioner may adjust so that the distance between the power transmitter and the power receiver is longer in the non-power-transmission time than in the power-transmission time.

Further, in the agitation apparatus, the positioner may bring the power transmitter and the power receiver into contact with each other or close to each other at the power-transmission time.

Further, in the agitation apparatus, the power receiver may be arranged on a different member from a member on which the power transmitter is arranged.

Further, in the agitation apparatus, the sound wave generator and the power receiver may be substantially fixed to the vessel, and the power transmitter is arranged at a position so as to move relative to the vessel.

Further, in the agitation apparatus, the sound wave generator may be arranged on a side surface of the vessel.

Further, in the agitation apparatus, the power transmitter may be arranged horizontally opposing to the sound wave generator.

Further, in the agitation apparatus, the sound wave generator may be arranged on a bottom surface of the vessel.

Further, in the agitation apparatus, the power transmitter may be arranged vertically opposing to the sound wave generator.

Further, in the agitation apparatus, the power transmitter and the power receiver may be connected by a cable.

Further, in the agitation apparatus, the power transmitter and the power receiver may be connected by radio via antennas.

Further, in the agitation apparatus, the power transmitter may transmit power to the power receiver when an antenna on a power transmission side is placed opposite to an antenna of a power reception side of the power receiver.

Further, in the agitation apparatus, the vessel may be formed of an optically transparent material and have one side surface, part of which is used as a photometric window.

Further, in the agitation apparatus, the power receiver may be arranged on a side surface on which the photometric window is provided at a position where the photometric window is not arranged.

Further, in the agitation apparatus, the power receiver may be arranged on a surface which is different from the surface on which the photometric window is arranged.

Further, in the agitation apparatus, the sound wave generator may be an interdigital transducer of a surface-acoustic-wave element that generates surface acoustic waves according to an applied high-frequency alternate-current electric field.

Further, in the agitation apparatus, the vessel may include plural vessels.

Further, in the agitation apparatus, the vessel may have plural retaining portions to retain the liquid.

Further, in the agitation apparatus, the power receiver may include plural power receivers.

Further, a vessel according to another aspect of the present invention agitates retained liquid using power transmitted from a power transmitter, and includes a power receiver which receives the power transmitted from the power transmitter and whose relative arrangement with respect to the power transmitter is changeable when an arrangement of at least one of the power transmitter and the power receiver is changed; and a sound wave generator that generates sound waves to agitate the liquid by converting the power received by the power receiver.

Further, an analysis according to still another aspect of the present invention analyzes reaction liquid by agitating and causing a reaction of a liquid sample including a specimen and a reagent retained in a vessel, and includes the agitation apparatus according to the present invention.

Further, an analysis apparatus according to still another aspect of the present invention analyzes reaction liquid by agitating and causing a reaction of a liquid sample including a specimen and a reagent retained in a vessel on which a sound wave generator that generates sound waves is integrally formed, and the sound wave generator generates the sound waves at least when the liquid sample is introduced into the vessel, when the liquid sample introduced into the vessel is agitated, when the liquid sample is transferred to an outlet of the vessel, when the liquid sample transferred to the outlet is discharged from the vessel, or when the liquid sample is dried.

Further, an agitation apparatus according to still another aspect of the present invention agitates a liquid using sound waves, and includes a liquid retaining portion that retains the liquid; an opening that is connected to the liquid retaining portion and introduces the liquid into the liquid retaining portion or discharges the liquid to an outside; and a sound wave generator that generates sound waves when the liquid retained in the liquid retaining portion is agitated and when the liquid is introduced into the liquid retaining portion through the opening or discharged through the opening.

Further, an agitation apparatus according to still another aspect of the present invention agitates a liquid using sound waves, and includes a liquid retaining portion that retains the liquid; an opening that is connected to the liquid retaining portion and introduces the liquid to the liquid retaining portion or discharges the liquid to an outside; and a sound wave generator that generates the sound waves when the liquid is in contact with a neighborhood of the opening.

Further, an analysis apparatus according to still another aspect of the present invention includes a vessel retaining a liquid including a specimen and a reagent and a sound wave generator formed integrally with the vessel and generating sound waves, the analysis apparatus analyzing the specimen by causing reaction between the specimen and the reagent, and the sound wave generator generates the sound waves, in addition to a time when the liquid including the specimen and the reagent is agitated, at least when the specimen, the reagent, or cleaning liquid is introduced into the vessel, or when the specimen, the reagent, or the cleaning liquid is discharged from the vessel.

Effect of the Invention

An agitation apparatus, a vessel, and an analysis apparatus including the agitation apparatus according to the present invention are advantageous in that they realize excellent energy transmission efficiency, simplified configuration, downsizing, and easy maintenance work.

Further, in the agitation apparatus, even when the capacity of the liquid retaining portion is made extremely small so as to make the area of the opening, through which the liquid is introduced into the liquid retaining portion and discharged from the liquid retaining portion, small, the sound wave generator generates the sound waves so as to overcome the influence of the surface tension of the liquid, whereby the liquid can be introduced into and discharged from the liquid retaining portion easily even when the opening has a small area.

Further, in the agitation apparatus, even when the capacity of the liquid retaining portion is made extremely small so as to make the area of the opening, through which the liquid is introduced into the liquid retaining portion and discharged from the liquid retaining portion, small, the sound waves generated from the sound wave generator is directed to the liquid while the liquid is in contact with the small-area opening and clogs the opening according to the surface tension, whereby the liquid in contact with the neighborhood of the opening is introduced into the liquid retaining portion or discharged from the liquid retaining portion easily.

Further, in the analysis apparatus, since the sound wave generator generates the sound wave not only when the liquid such as specimen and reagent to be analyzed is introduced into the vessel or discharged from the vessel, but also when the cleaning liquid is introduced into or discharged from the vessel, whereby the introduction and the discharge of the cleaning liquid into and from the vessel can be performed easily.

EXPLANATIONS OF LETTERS OR NUMERALS

Figure 1:
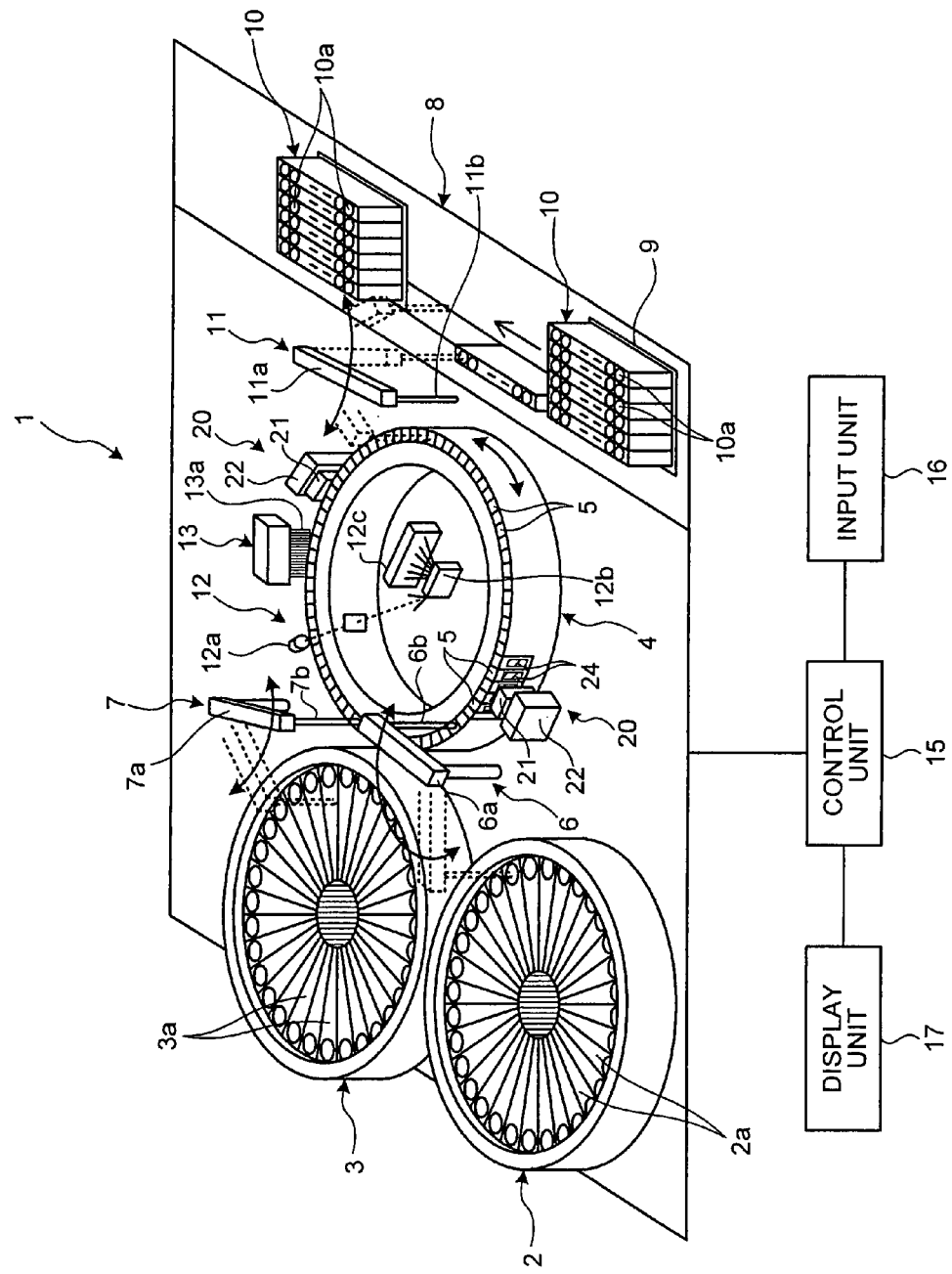
FIG. 1 shows a first embodiment of the present invention, and is a schematic configuration diagram of an automatic analysis apparatus including an agitation apparatus according to the first embodiment.

1 Automatic analysis apparatus
2, 3 Reagent table
2*a*, 3*a* Reagent vessel
4 Reaction table
4*a* Storage recess
5 Reaction vessel
5*a* Retaining portion
5*b* Photometric window
5*c* Side wall
5*d* Bottom wall
5*e* Depressed portion
5*f* Opening
6, 7 Reagent-dispensing mechanism
8 Specimen-vessel transfer mechanism
9 Feeder
10 Rack
11 Specimen-dispensing mechanism
11*a* Arm
11*b* Probe
12 Analytical optical system
12*a* Light-emitting portion
12*b* Spectral portion
12*c* Light-receiving portion
13 Washing mechanism
13*a* Nozzle
15 Control unit
16 Input unit
17 Display unit
20 Agitation apparatus
21 Power transmission element
21*a* Contact
21*b* Spring terminal
22 Positioning member
24 Surface-acoustic-wave element
24*a* Substrate
24*b* Sound wave generator
24*c* Electric terminal
24*d* Conductor circuit
25 Acoustic matching layer
30 Agitation apparatus
31, 39 Power transmission element
31*a* RF transmission antenna
31*b* Driving circuit
31*c* Controller
33, 35 Surface-acoustic-wave element
33*a*, 35*a* Substrate
33*b*, 35*b* Sound wave generator
33*c*, 35*c* Antenna
34, 37 Acoustic matching layer
36, 41 Surface-acoustic-wave element
36*a*, 41*a* Substrate
36*b*, 41*b* Sound wave generator
36*c* Antenna
43, 44 Surface-acoustic-wave element
43*a*, 44*a* Substrate
43*b*, 44*b* Sound wave generator 45, 50 Agitation apparatus
46, 51, 58 Power transmission element
46a, 51a, 58a RF transmission antenna
46b, 51b Driving circuit
46c, 51c, 58c Controller
47, 52, 57 Holder
47a, 52a Insertion portion
47b, 52b Side wall
48, 53, 54 Surface-acoustic-wave element
48a, 53a, 54a Substrate
48b, 53b, 54b Sound wave generator
48c, 53c, 54c Antenna
55, 65 Reaction vessel
55a, 65a Retaining portion
55c Side wall
55d, 65d Bottom wall
55f Opening
56, 66 Surface-acoustic-wave element
56a, 66a Substrate
56b, 66b Sound wave generator
56c Antenna
61 Suction nozzle
70 Agitation apparatus
71 Power transmission element
71a RF transmission antenna
71b Driving circuit
71c Controller
73 Surface-acoustic-wave element
73a Substrate
73b Sound wave generator
73c Antenna
75 Microplate
75a Main body
75b Well
75c Bottom surface
75d Vertex
Fcc Counterclockwise flow
Fcw Clockwise flow
Lc Cleaning liquid
Ls Liquid Sample
Lwf Waste fluid of cleaning liquid

BEST MODE(S) FOR CARRYING OUT THE INVENTION

First Embodiment

Figure 2:
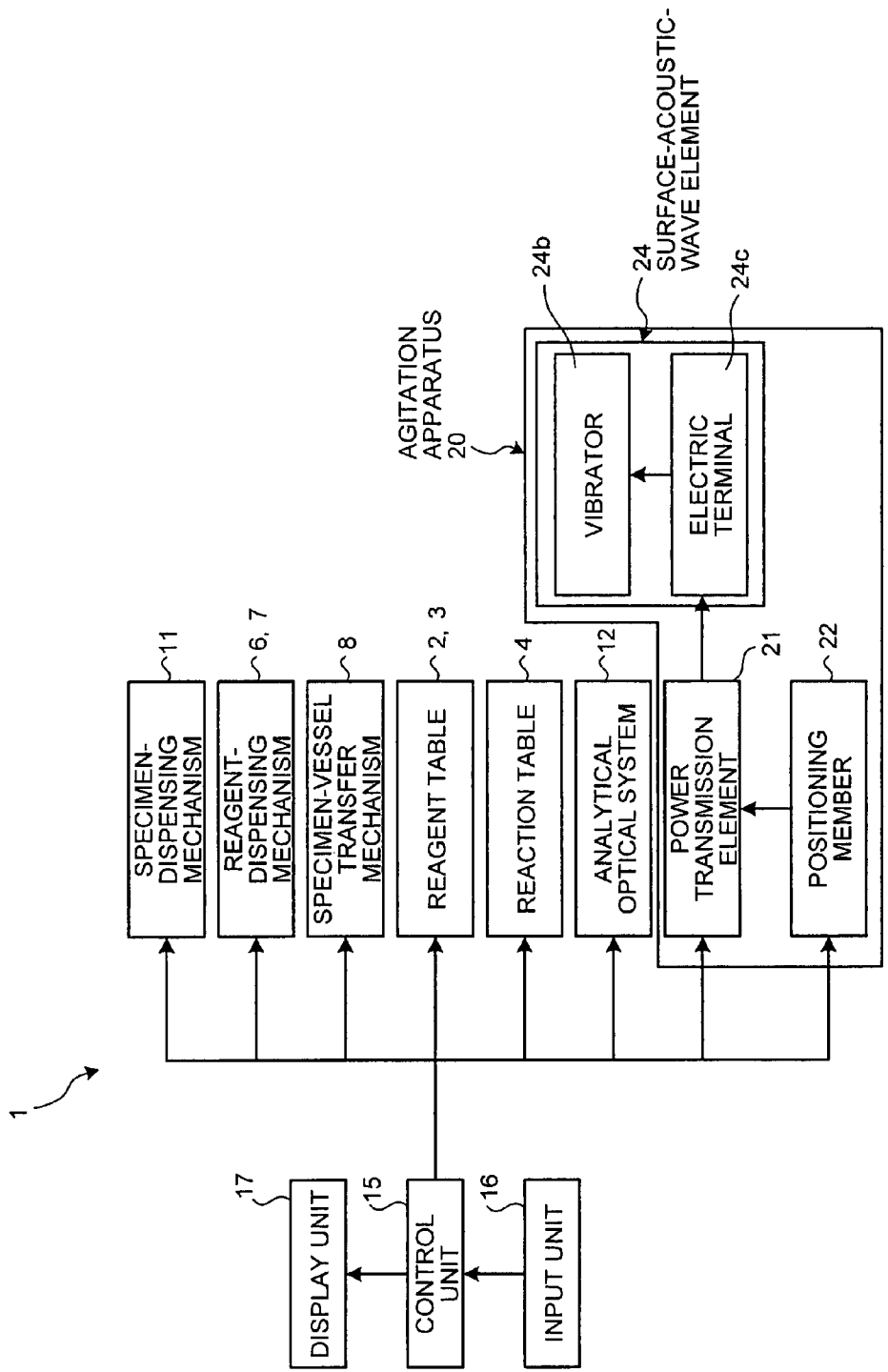
FIG. 2 is a block diagram of a configuration of the automatic analysis apparatus of FIG. 1.
Figure 3:
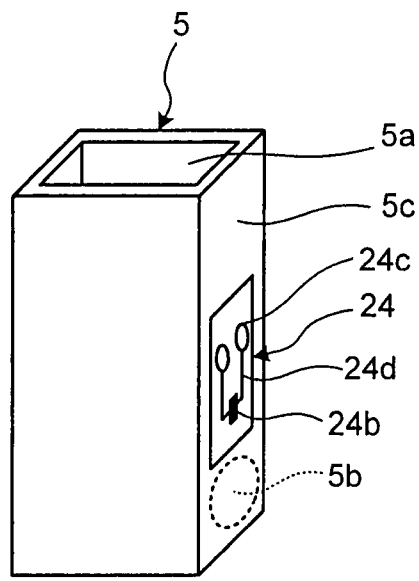
FIG. 3 is a perspective view of a vessel to which a surface-acoustic-wave element is attached and employed in the automatic analysis apparatus of FIG. 1.

An agitation apparatus, a vessel, and an analysis apparatus including the agitation apparatus according to a first embodiment of the present invention will be described in detail below with reference to the accompanying drawings. FIG. 1 is a schematic configuration diagram of an automatic analysis apparatus including the agitation apparatus. FIG. 2 is a block diagram of a configuration of the automatic analysis apparatus of FIG. 1. FIG. 3 is a perspective view of a vessel to which a surface-acoustic-wave element is attached and which is employed in the automatic analysis apparatus of FIG. 1.

An automatic analysis apparatus 1 includes reagent tables 2 and 3, a reaction table 4, a specimen-vessel transfer mechanism 8, an analytical optical system 12, a washing mechanism 13, a control unit 15, and an agitation apparatus 20 as shown in FIGS. 1 and 2.

As shown in FIG. 1, the reagent table 2 holds plural reagent vessels 2a circumferentially arranged, whereas the reagent table 3 holds plural reagent vessels 3a circumferentially arranged, and the reagent tables 2 and 3 are rotated by a driving unit (not shown) to transport the reagent vessels 2a and 3a in a circumferential direction.

In the reaction table 4, plural reaction vessels 5 are arranged along a circumferential direction as shown in FIG. 1. The reaction table 4 is rotated in a clockwise or counterclockwise direction as shown by an arrow by a driving unit (not shown) to transport the reaction vessels 5. Reagent-dispensing mechanisms 6 and 7 arranged close to the reaction vessel 5 dispense the reagent in each of the reagent vessels 2a and 3a on the reagent tables 2 and 3 to the reaction vessel 5. The reagent-dispensing mechanisms 6 and 7 respectively include probes 6b and 7b in arms 6a and 7a which rotate in directions of arrows in a horizontal plane to dispense the reagent, and further include a washer (not shown) that washes the probes 6b and 7b with washing water.

The reaction vessel 5 is, as shown in FIG. 3, a rectangular-tube-like vessel which is formed of an optically transparent material, and has a retaining portion 5a for retaining a liquid, and includes an integrally formed surface-acoustic-wave element 24 on one of plural side walls 5c. The reaction vessel 5 is made of a material which transmits at least 80% of light included in an analytical light (340 to 800 nm) emitted from the analytical optical system 12 described later. For example, the reaction vessel 5 is made of glass such as heat-resistant glass, synthetic resin such as cyclic olefin and polystyrene. In the reaction vessel 5, a portion enclosed by a dotted line and located below and adjacent to a portion where the surface-acoustic-wave element 24 is attached is utilized as a photometric window 5b which transmits the analytic light mentioned above. Further, the reaction vessel 5 is set in the reaction table 4 with the surface-acoustic-wave element 24 facing outward.

The specimen-vessel transfer mechanism 8 is a transfer unit which transfers plural racks 10 arranged on a feeder 9 one by one along a direction of an arrow as shown in FIG. 1, and advances the rack 10 stepwise. The rack 10 holds plural specimen vessels 10a each retain a specimen. Whenever the stepwise advancement of the rack 10 which is transferred by the specimen-vessel transfer mechanism 8 is stopped, a specimen-dispensing mechanism 11 having an arm 11a which rotates in a horizontal direction and a probe 11b dispenses the specimen in the specimen vessel 10a into each of the reaction vessels 5. The specimen-dispensing mechanism 11 has a washer (not shown) to wash the probe 11b with washing water.

The analytical optical system 12 serves to emit the analytical light (340 to 800 nm) for an analysis of the liquid sample obtained as a result of reaction between the reagent and the specimen in the reaction vessel 5, and includes a light-emitting portion 12a, a spectral portion 12b, and a light-receiving portion 12c, as shown in FIG. 1. The analytical light emitted from the light-emitting portion 12a passes through the liquid sample in the reaction vessel 5 and is received by the light-receiving portion 12c which is arranged at a position opposing to the spectral portion 12b. The light-receiving portion 12c is connected to the control unit 15.

The washing mechanism 13 washes the reaction vessel 5 after the analytical optical system 12 finishes the analysis, by aspirating and discharging the liquid sample in the reaction vessel 5 through a nozzle 13a, and repeatedly injecting and aspirating a cleaning liquid such as a washing agent and washing water through the nozzle 13a.

The control unit 15 controls an operation of each portion of the automatic analysis apparatus 1, and at the same time, analyzes components, concentration, and the like of the specimen based on absorbance of the liquid sample in the reaction vessel 5 based on quantity of light emitted from the light-emitting portion 12a and quantity of light received by the light-receiving portion 12c. For example, a micro computer is employed as the control unit 15. The control unit 15 is, as shown in FIGS. 1 and 2, connected to an input unit 16 such as a keyboard, and a display unit 17 such as a display panel.

Figure 4:
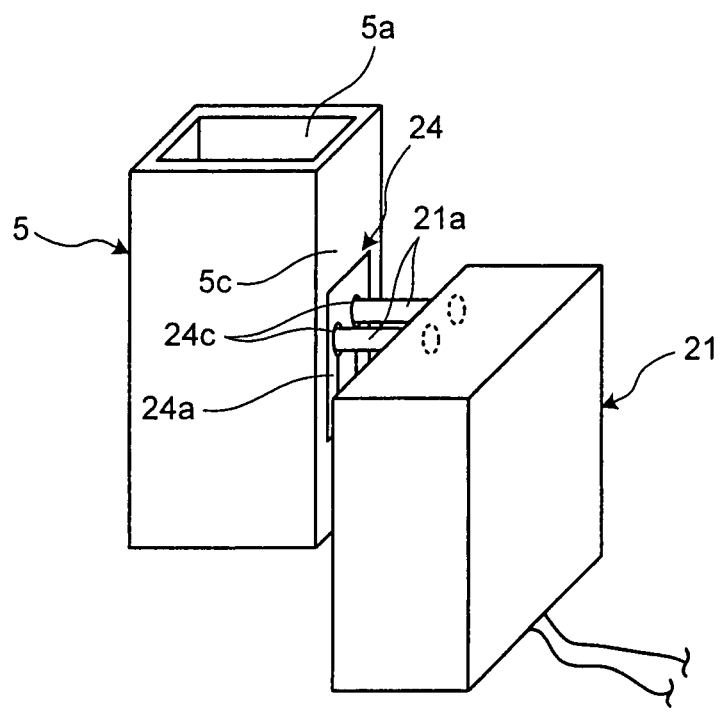
FIG. 4 is a perspective view of a power transmission element and the surface-acoustic-wave element of the vessel in contact with each other through contacts of the power transmission element and electric terminals of the surface-acoustic-wave element.

The agitation apparatus 20 includes, as shown in FIGS. 1 and 2, a power transmission element 21 and the surface-acoustic-wave element 24. The power transmission elements 21 are arranged at opposing positions on an outer circumferentia of the reaction table 4, so that the power transmission element 21 is placed opposite to the reaction vessel 5 in a horizontal direction; and the power transmission element 21 is a power transmitter which transmits approximately a few MHz to a few hundreds MHz power supplied from a high-frequency alternate-current power supply to the surface-acoustic-wave element 24. The power transmission element 21 includes a driving circuit and a controller, and has brush-like contacts 21a respectively touching electric terminals 24c of the surface-acoustic-wave element 24, as shown in FIG. 4. As shown in FIG. 1, the power transmission element 21 is supported by a positioning member 22. When the rotation of the reaction table 4 stops, power is transmitted from the contact 21a to the electric terminal 24c.

An operation of the positioning member 22 is controlled by the control unit 15, and the positioning member 22 serves to adjust relative arrangement of the power transmission element 21 and the electric terminal 24c in the circumferential direction and the radial direction of the reaction table 4 at a time of power transmission from the power transmission element 21 to the electric terminal 24c by moving the power transmission element 21. For example, a biaxial stage is employed as the positioning member 22. Specifically, in a non-power-transmission time, during which the reaction table 4 rotates and the power is not transmitted from the power transmission element 21 to the electric terminal 24c, the operation of the positioning member 22 is stopped, and the power transmission element 21 and the electric terminal 24c are kept at a predetermined distance away from each other. In a power-transmission time, during which the reaction table 4 stops and the power is transmitted from the power transmission element 21 to the electric terminal 24c, the positioning member 22 operates under the control of the control unit 15 and moves the power transmission element 21 so as to adjust the positions of the power transmission element 21 and the electric terminal 24c in the circumferential direction of the reaction table 4 so that the power transmission element 21 opposes the electric terminal 24c, thereby bringing the power transmission element 21 in close contact with the electric terminal 24c and making the contact 21a and the electric terminal 24c contact with each other, and thus determines the relative arrangement of the power transmission element 21 and the electric terminal 24c.

The agitation apparatus 20 may use the control unit 15 of the automatic analysis apparatus 1 as a positioning unit, and control a driving unit such as a motor that drives the rotation of the reaction table 4 by the control unit 15 so as to adjust the relative arrangement of the power transmission element 21 and the electric terminal 24c along the circumferential direction of the reaction table 4. It is sufficient if the positioning member 22 can adjust the relative arrangement of the power transmission element 21 and the electric terminal 24c at least in the circumferential direction of the reaction table 4 so that the power transmission element 21 and the electric terminal 24c oppose with each other. The relative arrangement of the power transmission element 21 and the electric terminal 24c is detected by a reflection sensor arranged at the side of the power transmission element 21, with the use of reflection from a reflector arranged at a specific position on the reaction vessel 5 or the surface-acoustic-wave element 24, for example. Data on the detected relative arrangement is input into the control unit 15.

Figure 5:
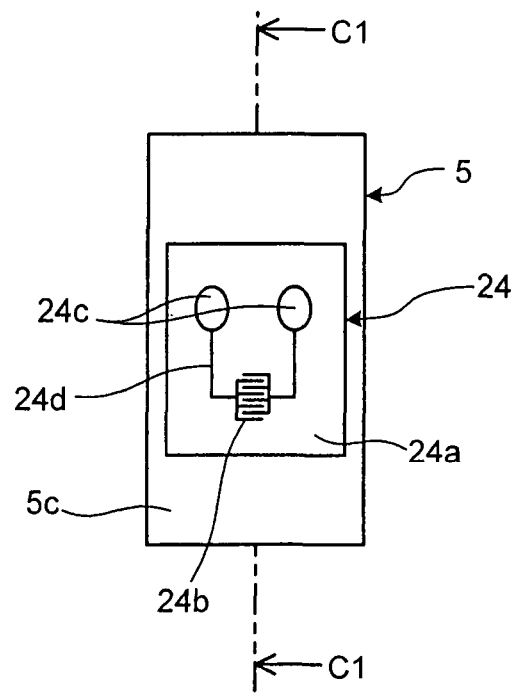
FIG. 5 is a side view of the vessel of FIG. 4 viewed from a side surface with the surface-acoustic-wave element.
Figure 6:
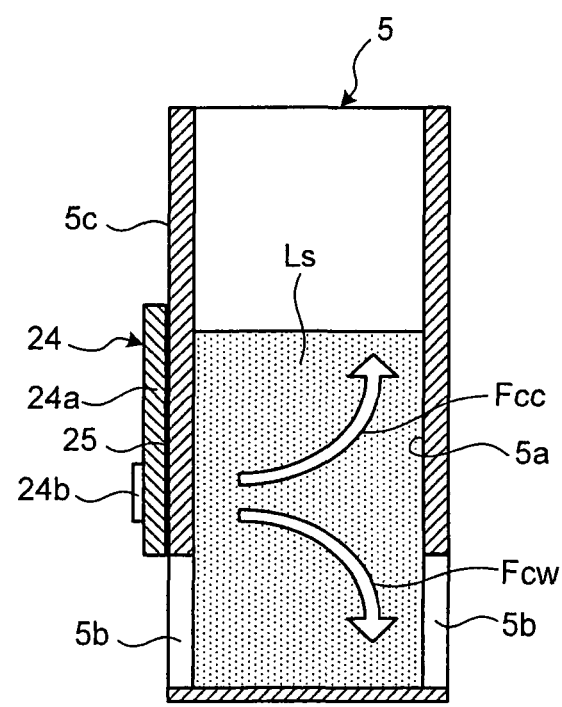
FIG. 6 is a sectional view of the vessel along line C1-C1 of FIG. 5.

The surface-acoustic-wave element 24 includes a sound wave generator 24b including interdigital transducers (IDT) arranged on a surface of a substrate 24a, as shown in FIGS. 3 and 5. The sound wave generator 24b is a sound-wave generator which converts the power transmitted from the power transmission element 21 into surface acoustic waves (ultrasound waves). Plural interdigital transducers are arranged in a vertical direction on the side wall 5c of the reaction vessel 5 as shown in FIG. 5 so that the surface acoustic waves (ultrasound waves) are generated in the vertical direction. In other words, the surface-acoustic-wave element 24 is attached onto the side wall 5c of the reaction vessel 5 so that the plural interdigital transducers of the sound wave generator 24b are arranged in the vertical direction when the reaction vessel 5 is set in the automatic analysis apparatus 1. The sound wave generator 24b is connected through a conductor circuit 24d to the electric terminal 24c that serves as a power receiver. The surface-acoustic-wave element 24 is attached onto the side wall 5c of the reaction vessel 5 with an acoustic matching layer 25 (see FIG. 6) of epoxy resin or the like posed therebetween, while the sound wave generator 24b, the electric terminal 24c, and the conductor circuit 24d are kept facing outward.

The surface-acoustic-wave element 24 including the electric terminal 24c as the power receiver is arranged at a portion other than the photometric window 5b portion on the same side surface of the reaction vessel 5 as the side where the photometric window 5b is arranged as shown in FIG. 3, so that the photometry of the analytical optical system 12 is not obstructed. Since the surface-acoustic-wave element 24 employs the interdigital transducers (IDT) as the sound wave generator 24b, the surface-acoustic-wave element 24 can be made to have a simplified configuration and a small size. The sound wave generator 24b may employ a Lead Zirconate Titanate (PZT) in place of the interdigital transducers (IDT).

In the automatic analysis apparatus 1 having the above-described configuration, the reagent-dispensing mechanisms 6 and 7 sequentially dispense the reagent from the reagent vessels 2a and 3a to the plural reaction vessels 5 that are transferred in the circumferential direction along with the rotation of the reaction table 4. After the reagent is dispensed into the reaction vessel 5, the specimen-dispensing mechanism 11 sequentially dispenses the specimen from the plural specimen vessels 10a held in the rack 10. Every time the reaction table 4 is stopped, the reagent and the specimen dispensed into the reaction vessel 5 are sequentially agitated by the agitation apparatus 20 and undergo reaction. When the reaction table 4 starts rotating again, the reaction vessel 5 passes through the analytical optical system 12. Thereupon, the light-receiving portion 12c performs photometry of the liquid sample in the reaction vessel 5. Then, the control unit 15 analyzes the components, concentration, and the like. After the analysis is completed, the washing mechanism 13 washes the reaction vessel 5, which is then employed for the analysis of the specimen again.

In the agitation apparatus 20, the power transmission element 21 transmits the power via the contact 21a to the electric terminal 24c when the reaction table 4 stops. Accordingly, the sound wave generator 24b of the surface-acoustic-wave element 24 is driven to induce surface acoustic waves. The induced surface acoustic waves propagate through the acoustic matching layer 25 and the side wall 5c of the reaction vessel 5, and leak out into the liquid sample which has close acoustic impedance. As a result, a counterclockwise flow Fcc and a clockwise flow Fcw are generated respectively at an upper portion and a lower portion in a liquid sample Ls in the reaction vessel 5, each originating from a position corresponding to the sound wave generator 24b as shown by arrows in FIG. 6. Two flows agitate the reagent and the specimen dispensed in the reaction vessel 5. Since the agitation apparatus 20 adjusts the positions using the positioning member 22 so as to bring the power transmission element 21 and the electric terminal 24c in close contact with each other, and to make the power transmission element 21 and the electric terminal 24c oppose to each other, the power transmission from the power transmission element 21 to the electric terminal 24c can be performed smoothly.

The surface-acoustic-wave element 24 is attached firmly to the side wall 5c of the reaction vessel 5 in an integral manner with the acoustic matching layer 25 (see FIG. 6) placed therebetween, and a bath retaining constant-temperature water is not employed. Therefore, the surface acoustic waves generated by the surface-acoustic-wave element 24 propagate through the acoustic matching layer 25 and the side wall 5c to the liquid sample, and are scarcely attenuated, thus the reaction vessel 5 has excellent energy transmission efficiency and a simplified configuration. As can be seen, the use of the reaction vessel 5 in the agitation apparatus 20 and the automatic analysis apparatus 1 allows for downsizing and simplified maintenance work compared with a conventional analysis apparatus which includes a bath retaining the constant-temperature water to maintain the temperature of the liquid sample at a constant level.

Figure 7:
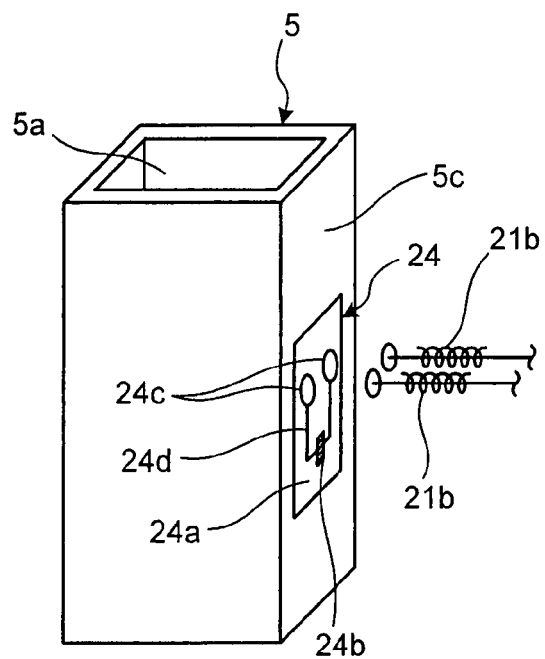
FIG. 7 is a perspective view of a modified example of the power transmission element including a spring terminal in place of the contact, and the vessel.

In the first embodiment, the agitation apparatus 20 is configured so that the power transmission element 21 contacts with the electric terminal 24c via the brush-like contact 21a to transmit power to the surface-acoustic-wave element 24. The agitation apparatus 20, however, may be configured so that at the power transmission to the surface-acoustic-wave element 24, the positioning member 22 having a rack and a pinion brings the power transmission element 21 closer to the reaction vessel 5 after the reaction table 4 is stopped, and makes a spring terminal 21b provided in the power transmission element 21 contact with the electric terminal 24c, as shown in FIG. 7. When the agitation apparatus 20 has the above configuration, the automatic analysis apparatus 1 keeps the power transmission element 21 away from the reaction vessel 5 using the positioning member 22 when the reaction table 4 is rotated for the transfer of the reaction vessel 5 so as to prevent the interference between the spring terminal 21b and the surface-acoustic-wave element 24.

Alternatively, the power transmission element 21 may be arranged inside the reaction table 4 together with the positioning member 22 in such a manner that at least the power transmission to the surface-acoustic-wave element 24 is allowed. The reaction vessel 5 may be set in the reaction table 4 with the surface where the surface-acoustic-wave element 24 is attached is kept facing inward.

Figure 8:
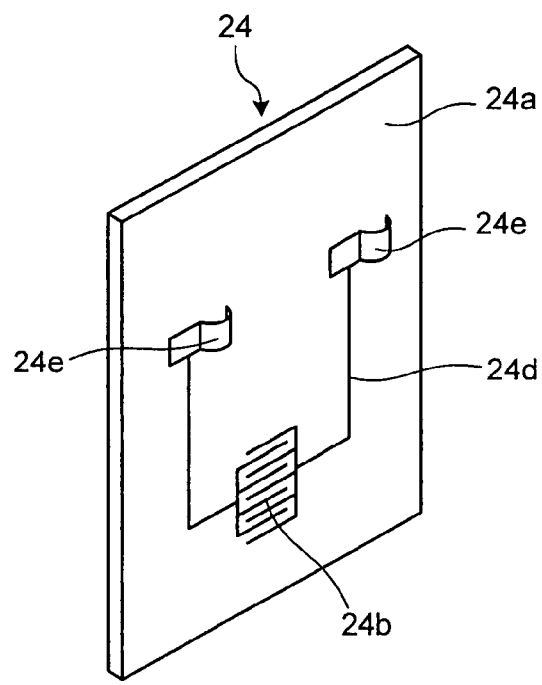
FIG. 8 is a perspective view of a modified example of the surface-acoustic-wave element.

On the other hand, the surface-acoustic-wave element 24 may be provided with a brush 24e formed with a flat spring deformed to have a curved protrusion in place of the electric terminal 24c as shown in FIG. 8. The power transmission element 21 may be provided with a terminal where the brush 24e touches as the reaction table 4 rotates. With such a configuration of the automatic analysis apparatus 1, when the reaction table 4 stops, the brush 24e integrally provided on the reaction vessel 5 comes into contact with the terminal of the power transmission element 21. Thus, the agitation apparatus 20 can transmit power from the power transmission element 21 to the surface-acoustic-wave element 24 via the brush 24e.

In the above description of the automatic analysis apparatus 1 according to the first embodiment, the positions of the power transmission element 21 and the electric terminal 24c, which is a power receiver, of the surface-acoustic-wave element 24 do not change unless the position of the power transmission element 21 is adjusted by the positioning member 22. The analysis apparatus of the present invention may be, however, a simple analysis apparatus in which the relative positions of the power transmission element 12 and the electric terminal 24c, which is the power receiver, of the surface-acoustic-wave element 24 change every time the reaction vessel is manually detached and attached for each measurement.

Second Embodiment

Figure 9:
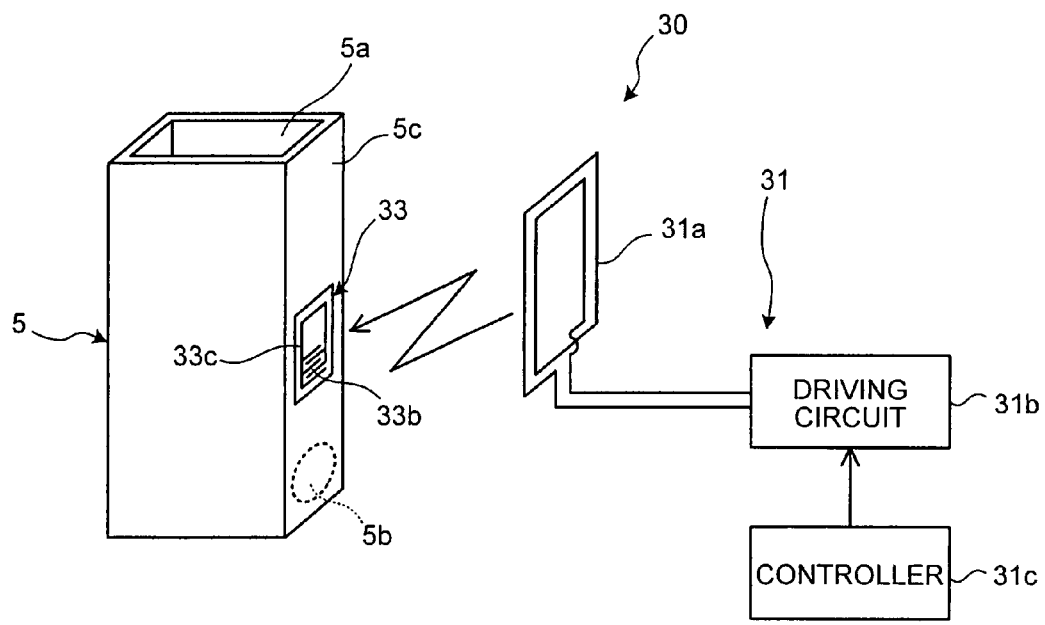
FIG. 9 shows an agitation apparatus and a vessel according to a second embodiment of the present invention, and is a perspective view of the vessel according to the second embodiment and a block diagram of a configuration of the agitation apparatus.
Figure 10:
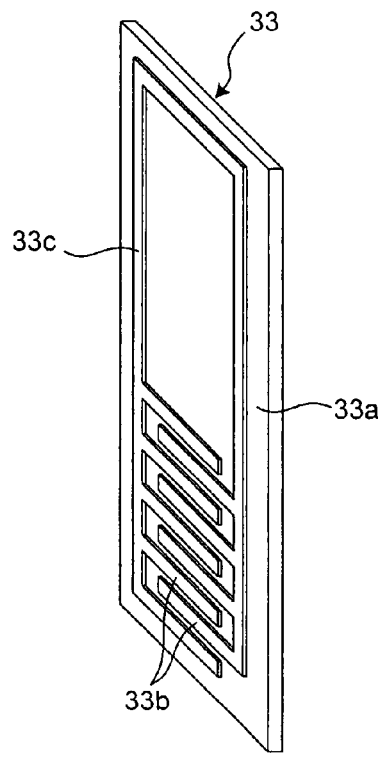
FIG. 10 is a perspective view of a surface-acoustic-wave element attached to the vessel in the agitation apparatus of FIG. 9.

An agitation apparatus, a vessel, and an analysis apparatus including the agitation apparatus according to a second embodiment of the present invention will be described in detail below with reference to the accompanying drawings. The agitation apparatus of the first embodiment transmits the power by bringing the power transmission element and the electric terminal of the surface-acoustic-wave element in contact with each other; on the other hand, the second embodiment employs an antenna to achieve non-contact power transmission while the same automatic analysis apparatus 1 as that of the first embodiment is employed. FIG. 9 shows the agitation apparatus and the vessel according to the second embodiment of the present invention, and is a perspective view of the vessel of the second embodiment and a block diagram of a configuration of the agitation apparatus. FIG. 10 is a perspective view of a surface-acoustic-wave element which is attached to the reaction vessel in the agitation apparatus of FIG. 9.

An agitation apparatus 30 has a power transmission element 31 which serves as a power transmitter and a surface-acoustic-wave element 33, as shown in FIG. 9. The surface-acoustic-wave element 33 is attached to the side wall 5c, in which the photometric window 5b is formed, of the reaction vessel 5 in an integral manner.

The power transmission element 31 is supported by the positioning member 22 similarly to the power transmission element 21, so that the power transmission elements 31 are placed at opposing positions on the outer circumferentia of the reaction table 4 horizontally opposing to the reaction vessel 5. The power transmission element 31 is arranged opposite to the surface-acoustic-wave element 33, and includes an RF transmission antenna 31a, a driving circuit 31b, and a controller 31c. The power transmission element 31 transmits the power of an approximately few MHz to a few hundred MHz supplied from a high-frequency alternate-current power supply to the surface-acoustic-wave element 33 via the RF transmission antenna 31a as electric waves. When the power transmission element 31 is to transmit the power to the surface-acoustic-wave element 33, the positioning member 22 adjusts and determines the relative arrangement of the power transmission element 31 with respect to the reaction table 4 in a circumferential direction and a radial direction so that the RF transmission antenna 31a and the antenna 33c are opposing to each other. The relative arrangement of the RF transmission antenna 31a and the antenna 33c is detected with the use of, for example, a reflection sensor provided at the power transmission element 31 side and reflection from a reflector provided at a specific position on the reaction vessel 5 or the surface-acoustic-wave element 33.

Figure 11:
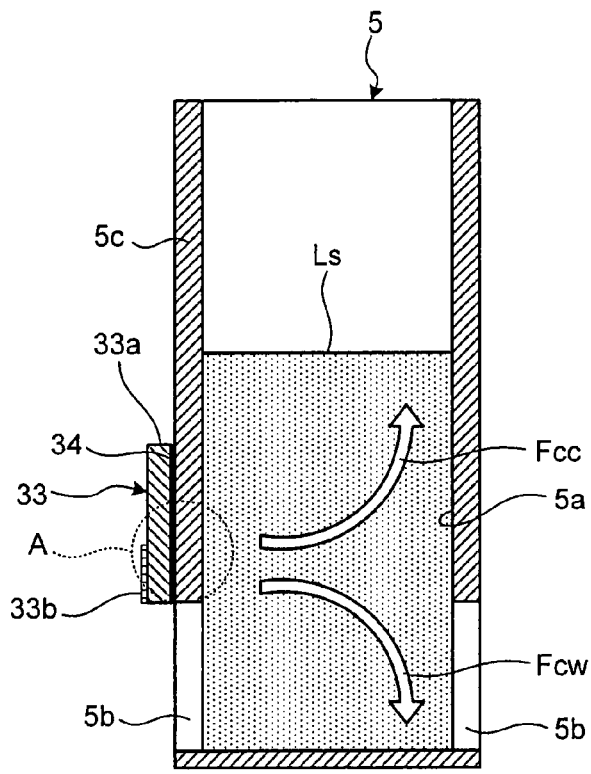
FIG. 11 is a sectional view of the vessel shown in FIG. 9.
Figure 12:
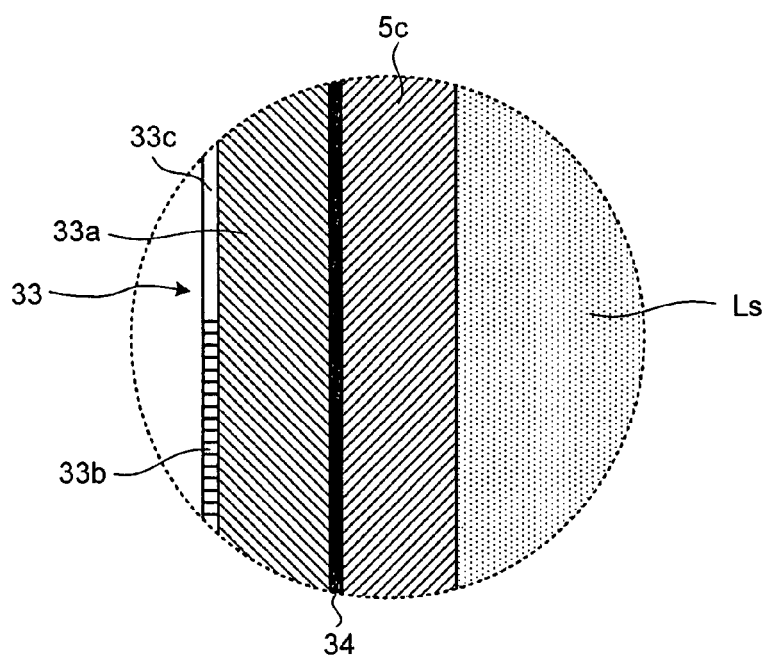
FIG. 12 is an enlarged view of an A portion of FIG. 11.

The surface-acoustic-wave element 33 includes a sound wave generator 33b including interdigital transducers (IDT) provided on the surface of a substrate 33a as an integral part of the antenna 33c as shown in FIG. 10. The surface-acoustic-wave element 33 is attached to the side wall 5c of the reaction vessel 5 with an acoustic matching layer 34 (see FIGS. 11 and 12) made of epoxy resin or the like posed therebetween, while the sound wave generator 33b and the antenna 33c are kept facing outward. As shown in FIG. 9, the surface-acoustic-wave element 33 is attached to the reaction vessel 5 so that the plural interdigital transducers of the sound wave generator 33b are arranged in the vertical direction, and the antenna 33c is arranged in a position other than a position where the photometric window 5b is provided on the same side surface as the photometric window 5b is provided. Using the interdigital transducers (IDT) as the sound wave generator 33b, the surface-acoustic-wave element 33 is allowed to have a simplified configuration and a small size. The surface-acoustic-wave element 33 receives the electric waves transmitted from the power transmission element 31 to the antenna 33c to generate the surface acoustic waves (ultrasound waves) from the sound wave generator 33b according to the electromotive force caused by the resonance.

In the agitation apparatus 30 having the above-described configuration, the power transmission element 31 transmits the electric waves from the RF transmission antenna 31a when the reaction table 4 stops and the RF transmission antenna 31a and the antenna 33c come to oppose with each other. Then, the antenna 33c of the surface-acoustic-wave element 33 placed opposite to the power transmission element 31 receives the electric waves to generate the electromotive force by the resonance. In the agitation apparatus 30, the sound wave generator 33b generates the surface acoustic waves (ultrasound waves) according to the electromotive force, and the surface acoustic waves propagate through the acoustic matching layer 34 to the inside of the side wall 5c of the reaction vessel 5, and eventually leak out to the liquid sample which has a close acoustic impedance. As a result, a counterclockwise flow Fcc and a clockwise flow Fcw are generated respectively in an upper portion and a lower portion as shown by arrows of FIG. 11 in the liquid sample Ls in the reaction vessel 5, originating from a position corresponding to the sound wave generator 33b, whereby the dispensed reagent and the specimen are agitated.

As described above, the agitation apparatus 30 transmits the power in a non-contact manner from the power transmission element 31 to the surface-acoustic-wave element 33 attached to the reaction vessel 5 using the RF transmission antenna 31a and the antenna 33c. Therefore, similarly to the agitation apparatus 20 of the first embodiment, the agitation apparatus 30 realizes excellent energy transmission efficiency, and easy maintenance work, and further, the surface-acoustic-wave element 33 has more simplified and downsized configuration in comparison with that in the agitation apparatus 20, whereby the automatic analysis apparatus 1 can be further downsized.

Figure 13:
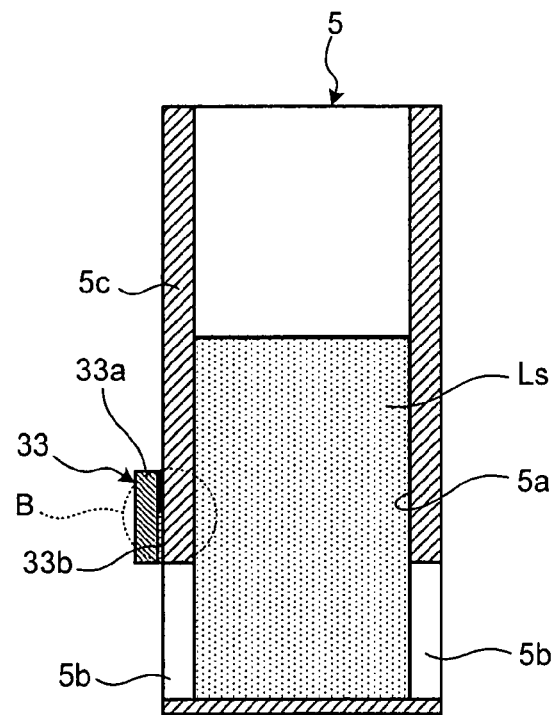
FIG. 13 is a sectional view showing an another manner of attachment of the surface-acoustic-wave element.
Figure 14:
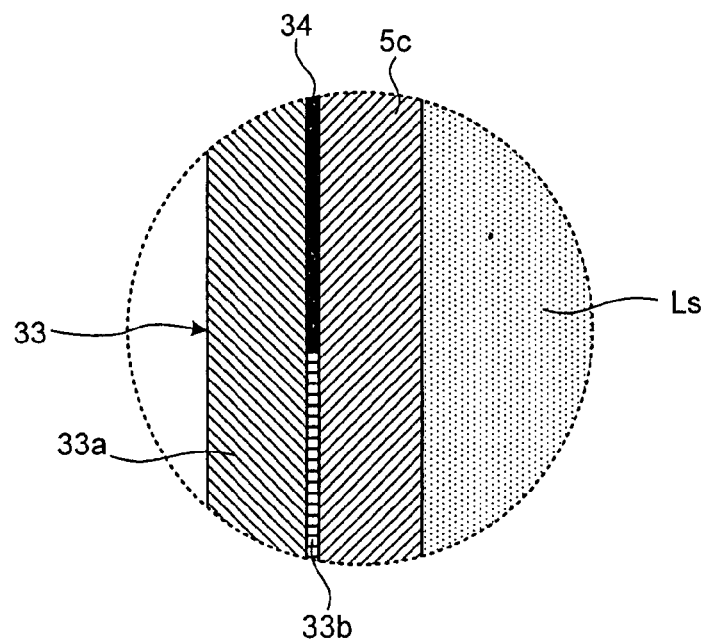
FIG. 14 is an enlarged view of a B portion of FIG. 13.

Since the surface-acoustic-wave element 33 employs the interdigital transducers (IDT) as the sound wave generator 33b, the configuration thereof is simplified, and in particular, a portion of the sound wave generator 33b can be made thin. Therefore, the surface-acoustic-wave element 33 may be attached to the side wall 5c with the sound wave generator 33b facing inward as shown in FIG. 13. As shown in FIG. 14, the acoustic matching layer 34 is placed between the surface-acoustic-wave element 33 and the side wall 5c. Thus, in the reaction vessel 5, the sound wave generator 33b, the antenna 33c, and the like of the surface-acoustic-wave element 33 are not exposed to the outside and protected by the substrate 33a, whereby the degradation of the surface-acoustic-wave element 33 can be suppressed in comparison with the surface-acoustic-wave element having the sound wave generator 33b, the antenna 33c, and the like arranged outside, and the long-term use can be realized.

Figure 15:
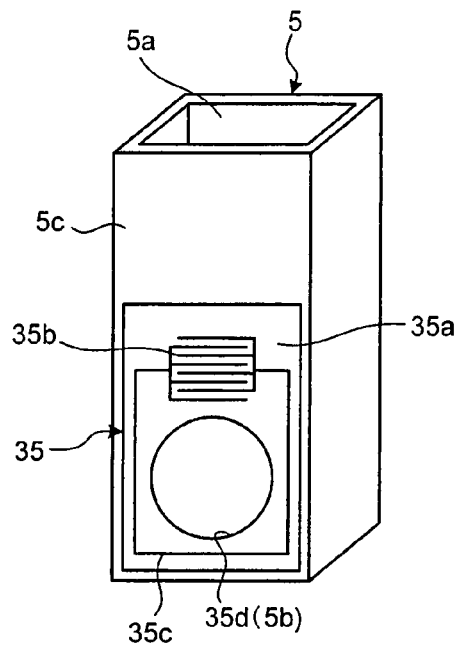
FIG. 15 is a perspective view of the vessel and shows another mode of the surface-acoustic-wave element.

In the agitation apparatus 30, the surface-acoustic-wave element 33 is arranged on the same side surface as that on which the photometric window 5b is arranged. In consideration of the analysis of the liquid sample by the analytic optical system 12 of the automatic analysis apparatus 1, however, the surface-acoustic-wave element 33 needs to be arranged at a portion other than the portion where the photometric window 5b is provided. However, since the reaction vessel 5 has a little capacity, an area where the surface-acoustic-wave element 33 can be arranged is limited. Therefore, as exemplified by a surface-acoustic-wave element 35 shown in FIG. 15, an opening 35d may be provided in a substrate 35a of a surface-acoustic-wave element at a position corresponding to the window 5b of the reaction vessel 5, and an antenna 35c may be arranged around the opening 35d and formed integrally with a sound wave generator 35b. The opening 35d is aligned with the position of the window 5b of the reaction vessel 5, and the surface-acoustic-wave element is attached to the reaction vessel 5 with the acoustic matching layer (not shown) of epoxy resin or the like placed therebetween. With the above configuration of the surface-acoustic-wave element 35, the antenna 35c is arranged at a portion other than the portion where the photometric window 5b is provided in the reaction vessel 5, and the plural interdigital transducers of the sound wave generator 35b are arranged in the vertical direction. Thus, regardless of the small capacity of the reaction vessel 5, an optical path for photometry by the analytic optical system 12 can be secured in the agitation apparatus 30.

Figure 16:
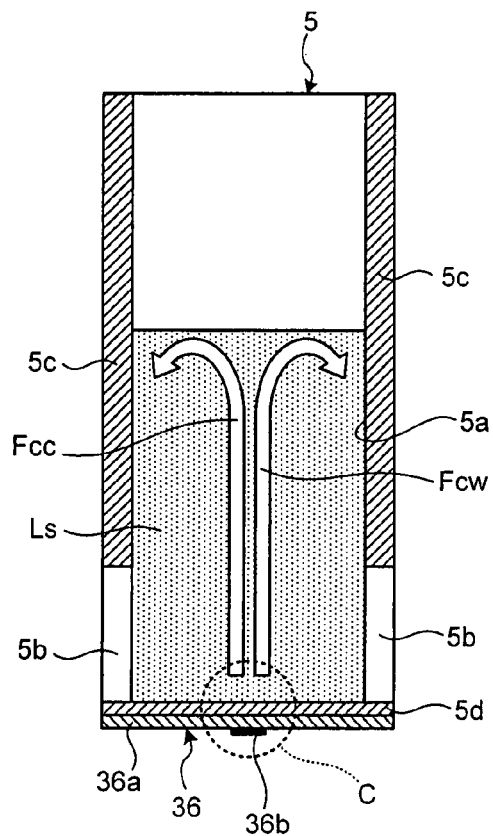
FIG. 16 is a sectional view of the vessel to whose bottom surface the surface-acoustic-wave element is attached.
Figure 17:
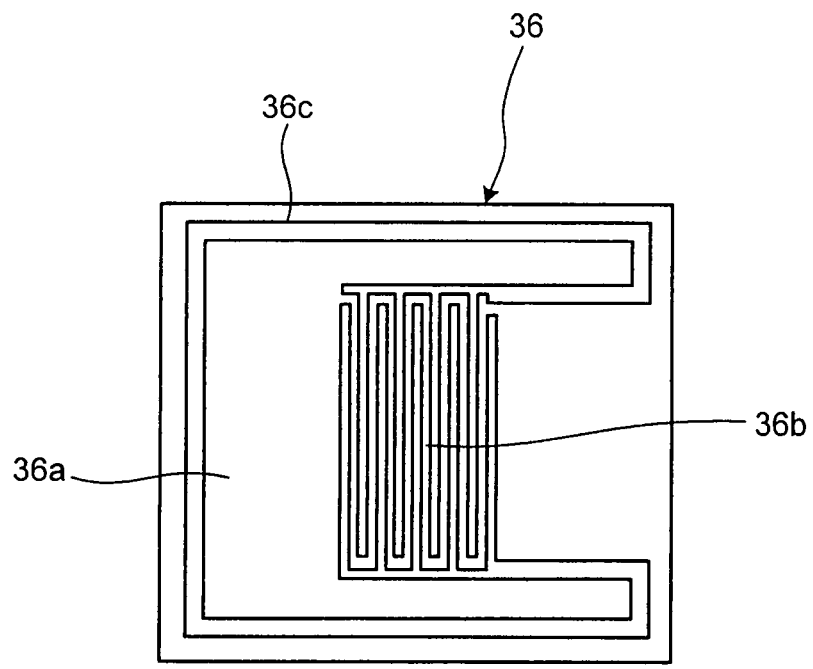
FIG. 17 is a view of the surface-acoustic-wave element of FIG. 16 viewed from the bottom surface of the vessel.
Figure 18:
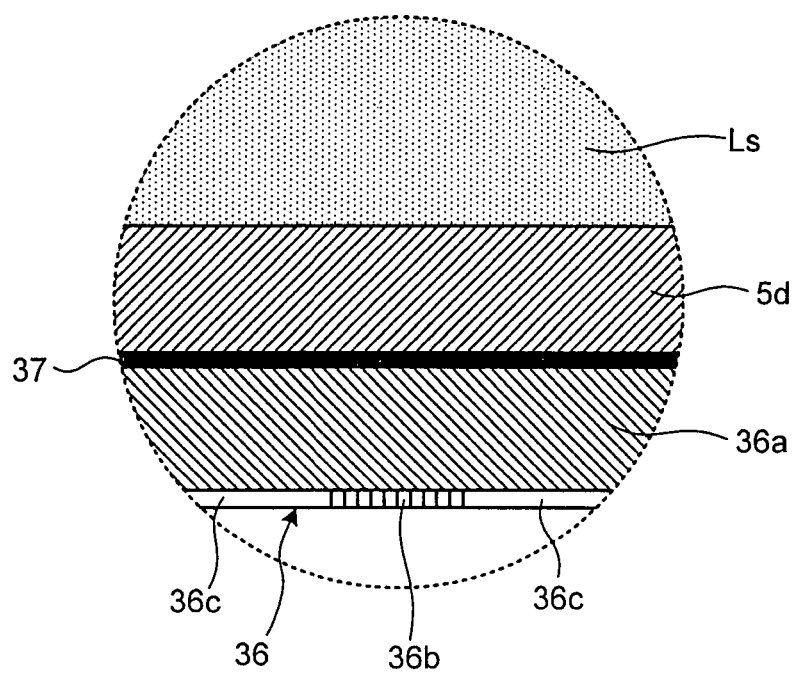
FIG. 18 is an enlarged view of a C portion of FIG. 16.

Further, since the agitation apparatus 30 can transmit the power in the non-contact manner, there is an increased degree of freedom with respect to the attachment position of the surface-acoustic-wave element on the reaction vessel 5. Hence, a surface-acoustic-wave element 36 may be attached to the bottom surface of a bottom wall 5d of the reaction vessel 5 as shown in FIG. 16, and not on the same side surface as that on which the photometric window 5b is provided. As shown in FIG. 17, in the surface-acoustic-wave element 36, a sound wave generator 36b including the interdigital transducers (IDT) is formed integrally with an antenna 36c which serves as a power receiver on the surface of a substrate 36a. As shown in FIG. 18, the surface-acoustic-wave element 36 is attached to the bottom surface of the bottom wall 5d via an acoustic matching layer 37 of epoxy resin or the like. Thus in the surface-acoustic-wave element 36, the plural interdigital transducers of the sound wave generator 36b are arranged in a horizontal direction. Therefore, a counterclockwise flow Fcc and a clockwise flow Fcw are generated respectively at the left side and the right side in the liquid sample Ls in the reaction vessel 5 originating from a position corresponding to the sound wave generator 36b as shown by arrows in FIG. 16, and the dispensed reagent and the specimen are agitated.

After the agitation and reaction of the reagent and the specimen, the light-receiving portion 12c of the automatic analysis apparatus 1 performs photometry of the liquid sample, and the control unit 15 analyzes the components, concentration, and the like of the liquid sample. After the analysis is finished, the reaction vessel 5 is washed by the washing mechanism 13 and employed for the analysis of the specimen again.

Figure 19:
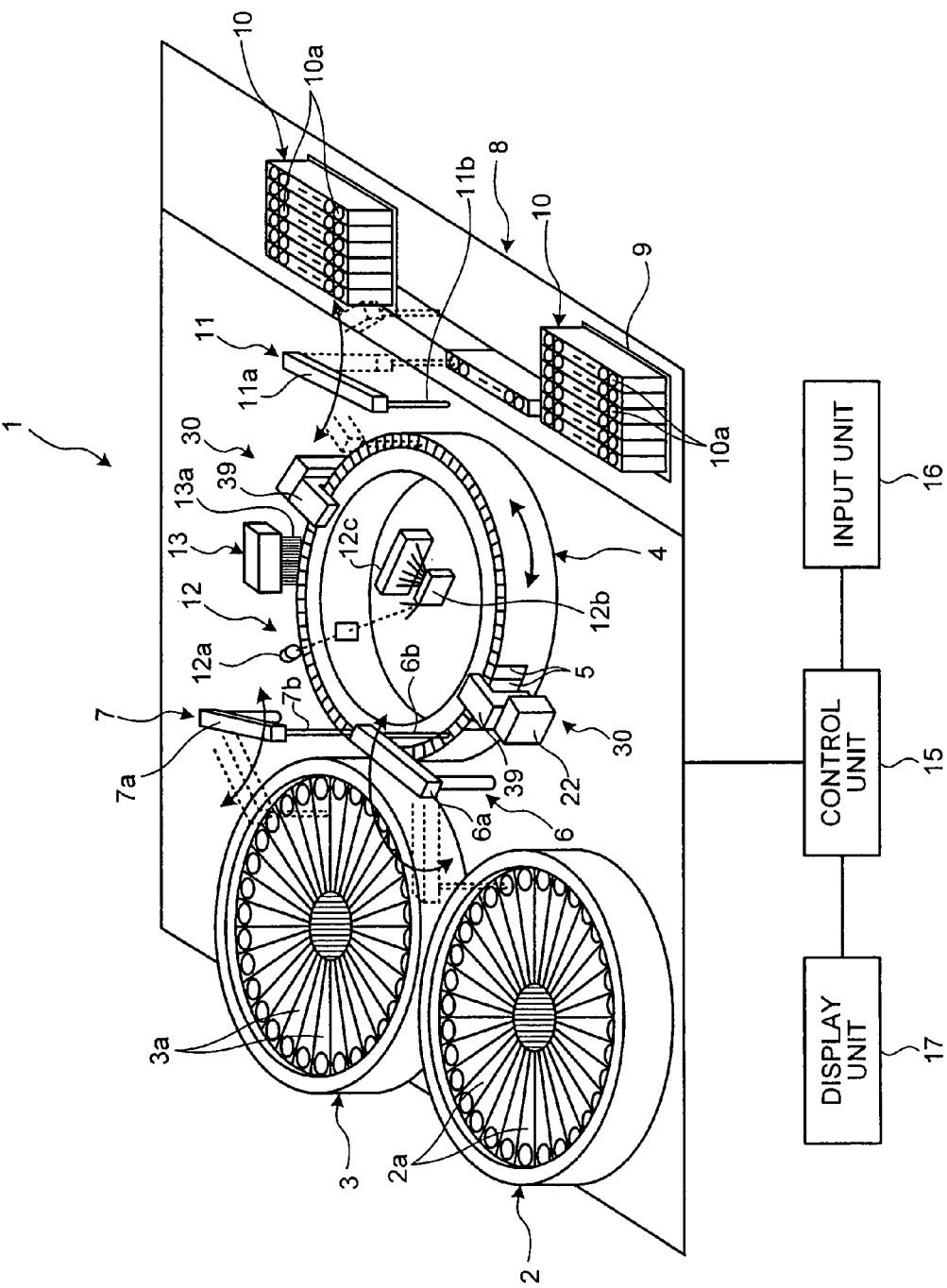
FIG. 19 is a schematic configuration diagram of an automatic analysis apparatus which is employed when the surface-acoustic-wave element is attached to the bottom surface of the vessel.

As described above, when the surface-acoustic-wave element 36 is attached to the bottom surface of the reaction vessel 5, the power transmission element that transmits power to the antenna 36c needs to be arranged at a position vertically opposing to the surface-acoustic-wave element 36. Therefore, in the automatic analysis apparatus 1, a power transmission element 39 supported by the positioning member 22 is formed so as to hang over the reaction vessel 5 on the reaction table 4 as shown in FIG. 19. Further, the power transmission element 39 is provided with an RF transmission antenna (not shown) on a bottom surface portion above the reaction vessel 5. The power transmission element 39 may be formed in such a size that one power transmission element 39 can transmit the power to the plural reaction vessels 5 arranged along the circumferential direction of the reaction table 4, and the RF transmission antenna (not shown) may be formed in a shape corresponding to the plural reaction vessels 5 as shown in FIG. 19. With the above-described configuration, the agitation apparatus 30 can agitate the liquid sample in plural reaction vessels 5 simultaneously. The power transmission element 39 supported by the positioning member 22 may be formed so as to protrude below the reaction vessel 5 of the reaction table 4 depending on the design of the automatic analysis apparatus 1, and the RF transmission antenna (not shown) may be provided below the bottom surface of the reaction vessel 5.

Figure 20:
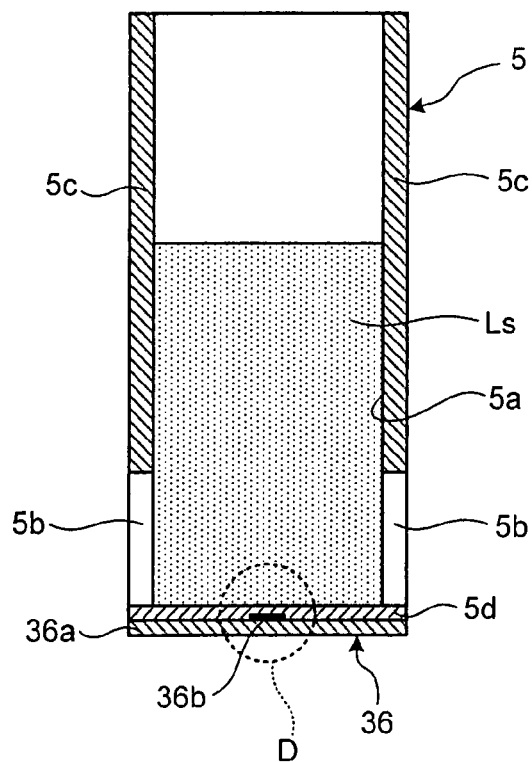
FIG. 20 is a sectional view of a reaction vessel to which the surface-acoustic-wave element is attached with a sound wave generator facing a bottom wall.
Figure 21:
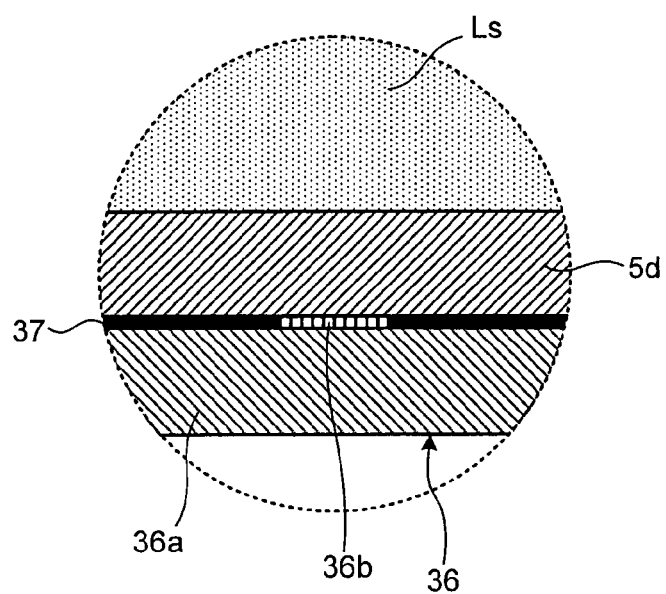
FIG. 21 is an enlarged view of a D portion of FIG. 20.

When the surface-acoustic-wave element 36 is arranged at the bottom surface of the bottom wall 5d, the surface-acoustic-wave element 36 may be attached to the reaction vessel 5 with the acoustic matching layer 37 placed therebetween while the sound wave generator 36b is kept facing toward the bottom wall 5d, as shown in FIGS. 20 and 21. With such a configuration, the sound wave generator 36b, the antenna (not shown), and the like of the surface-acoustic-wave element 36 are not exposed to the outside and protected by the substrate 36a, and therefore, compared with a configuration in which the sound wave generator 36b, the antenna, and the like are exposed to the outside, a longer-term use of the reaction vessel 5 is allowed.

Figure 22:
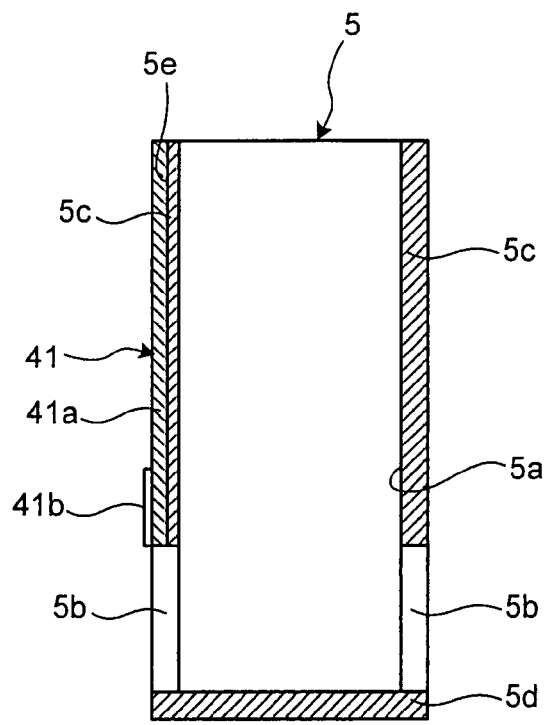
FIG. 22 is a sectional view showing another manner of attachment of the surface-acoustic-wave element to the vessel.
Figure 23:
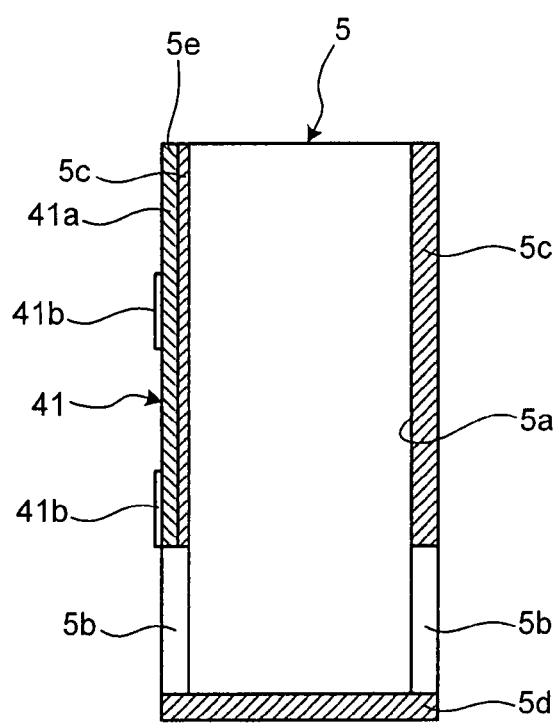
FIG. 23 is a sectional view of a modified example of the surface-acoustic-wave element of FIG. 22, having two sound wave generators.

Further, since the interdigital transducers (IDT) are employed as the sound wave generator, the surface-acoustic-wave element can be made to have a simplified configuration and a small size. Therefore, in the reaction vessel 5, the antenna of the surface-acoustic-wave element can be arranged at a portion other than the portion where the photometric window 5b is arranged; for example, a depressed portion 5e may be formed as a thinned upper portion of the side wall 5c and the surface-acoustic-wave element 41 may be attached at the depressed portion 5e with the acoustic matching layer (not shown) of epoxy resin or the like posed therebetween as shown in FIG. 22. In a surface-acoustic-wave element 41, a sound wave generator 41b including interdigital transducers (IDT) is formed integrally with the antenna (not shown) that serves as a power receiver on the surface of a substrate 41a. The surface-acoustic-wave element 41 may have two sound wave generators 41b as in the reaction vessel 5 shown in FIG. 23. With such a configuration, the agitation capability of the reaction vessel 5 is enhanced, and the liquid sample can be agitated in a short time even when a large volume of liquid sample is retained in the retaining portion 5a.

Figure 24:
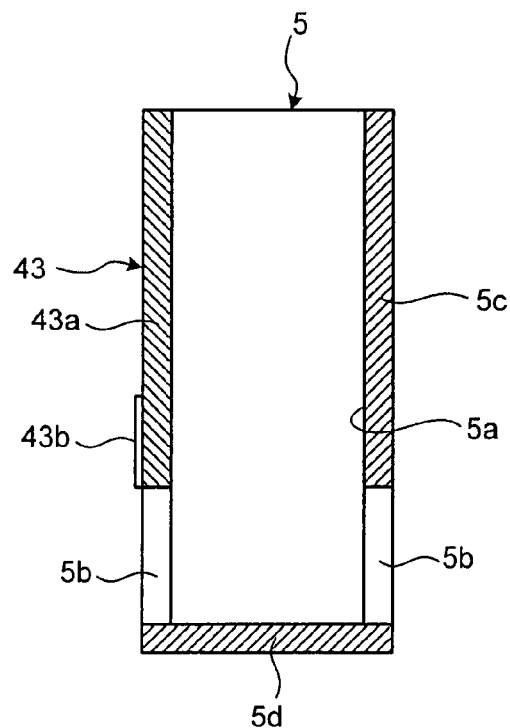
FIG. 24 is a sectional view of an example of the surface-acoustic-wave element, where the surface-acoustic-wave element is employed as a part of a side wall of the vessel.
Figure 25:
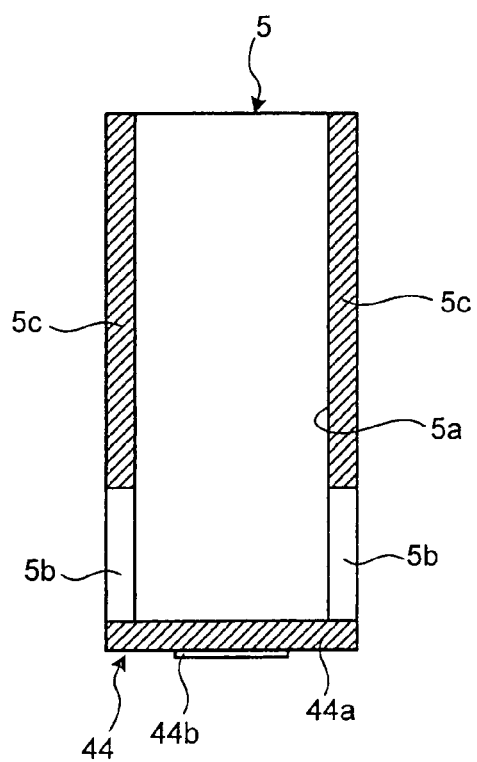
FIG. 25 is a sectional view of an example of the surface-acoustic-wave element, where the surface-acoustic-wave element is employed as a bottom wall of the vessel.

Further, since the surface-acoustic-wave element can be formed in a small size, a surface-acoustic-wave element 43 may be employed as a part of the side wall of the reaction vessel 5 as shown in FIG. 24, such that the surface-acoustic-wave element 43 is buried above the window 5b. In the surface-acoustic-wave element 43, a sound wave generator 43b including interdigital transducers (IDT) is formed integrally with the antenna (not shown) serving as a power receiver on the surface of a substrate 43a. Further, the reaction vessel 5 may employ a surface-acoustic-wave element 44 as the bottom wall as shown in FIG. 25. The surface-acoustic-wave element 44 includes a sound wave generator 44b including interdigital transducers (IDT) and an antenna (not shown) serving as a power receiver and formed integrally on the surface of a substrate 44a, and is attached to the reaction vessel 5 while the sound wave generator 44b is kept facing downward.

Figure 26:
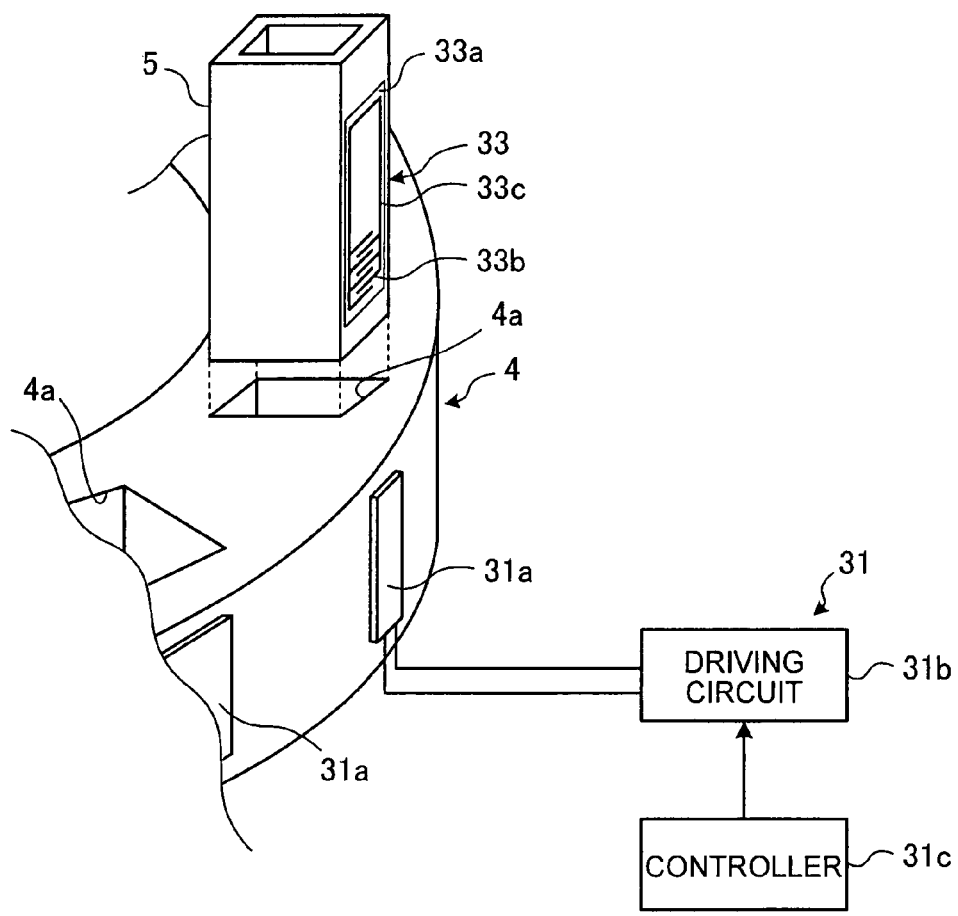
FIG. 26 is a perspective view of another example of a positioning unit which adjusts and determines relative arrangement of the power transmission element and a power receiver.
Figure 27:
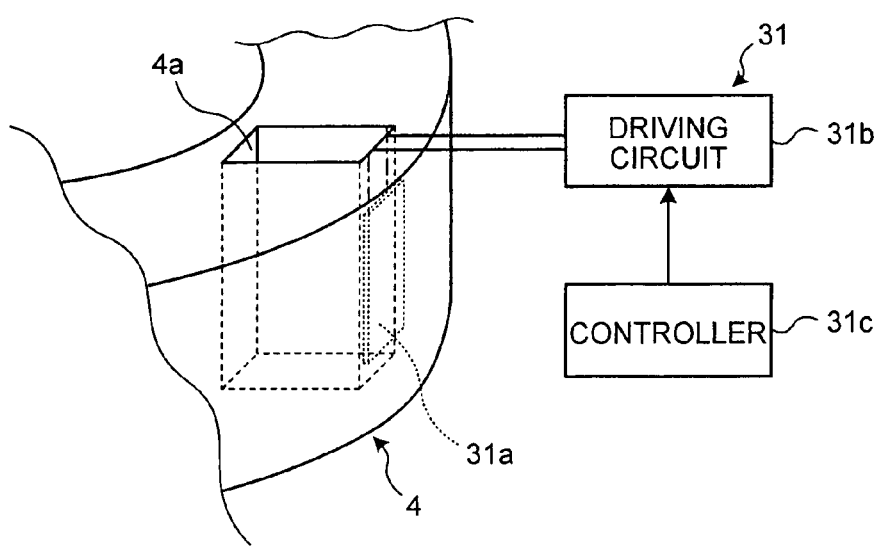
FIG. 27 is a perspective view of still another example of the positioning unit which adjusts and determines relative arrangement of the power transmission element and the power receiver.

The automatic analysis apparatus 1 may employ a storage recess 4a formed along a circumferential direction of the reaction table 4 as shown in FIG. 26 as a positioner that adjusts and determines the relative arrangement of the power transmission element 31 and the antenna 33c. The reaction vessel 5 may receive the power transmitted from the RF transmission antenna 31a attached on an outer side surface of the reaction table 4 with the antenna 33c of the surface-acoustic-wave element 33, and generates the surface acoustic waves (ultrasound waves) in the sound wave generator 33b due to the electromotive force generated by resonance. Further, when the RF transmission antenna 31a is arranged on an internal surface of the storage recess 4a as shown in FIG. 27, the power transmission loss can be minimized.

Third Embodiment

Figure 28:
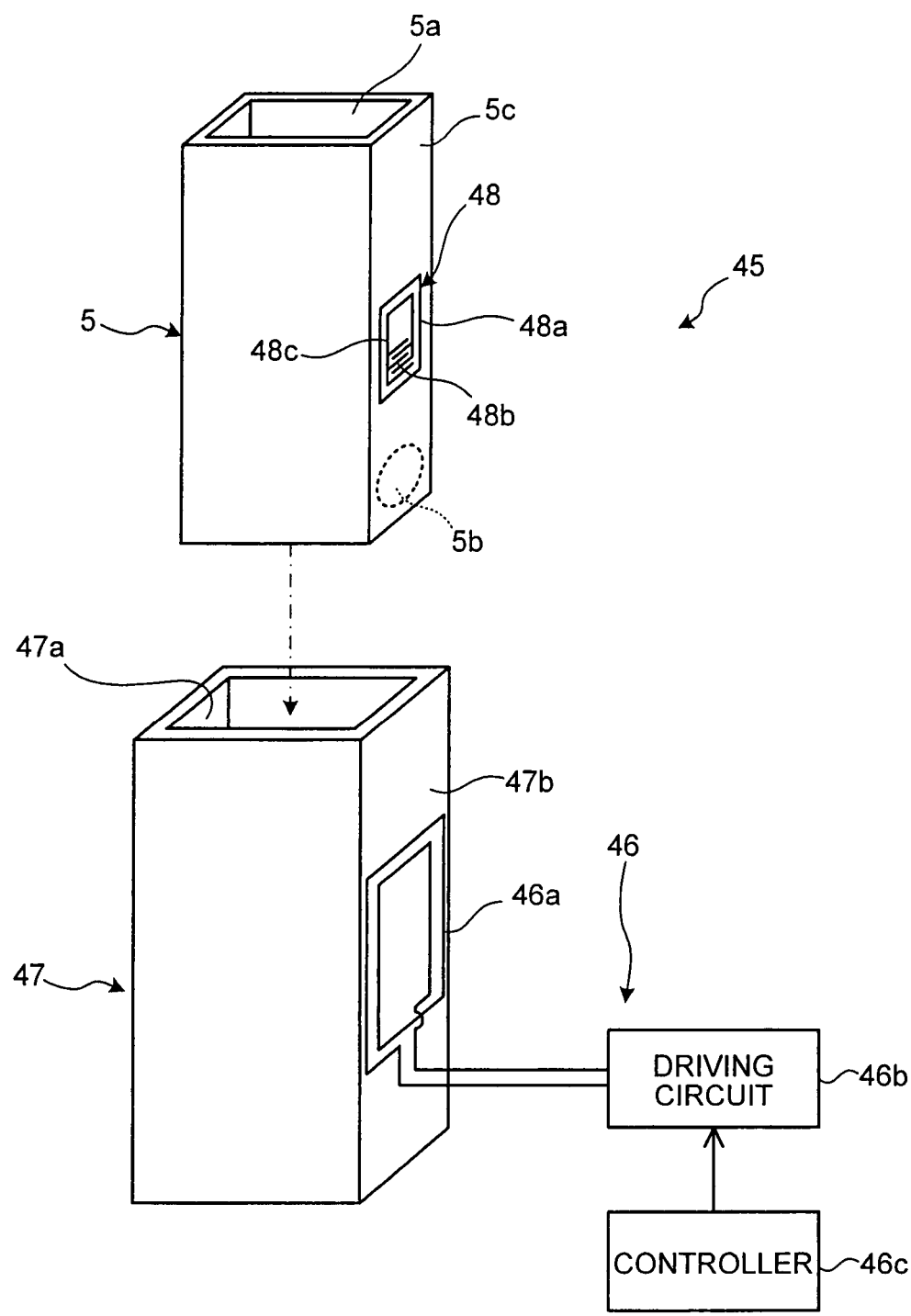
FIG. 28 shows an agitation apparatus and a vessel according to a third embodiment of the present invention, and is a perspective view of the vessel according to the third embodiment and a block diagram of a configuration of the agitation apparatus.

An agitation apparatus and a vessel according to a third embodiment of the present invention will be described in detail below with reference to the accompanying drawings. The agitation apparatus of the second embodiment adjusts and determines the relative arrangement of the power transmission element 31 and the antenna 33c by using the positioning member that moves the power transmission element. On the other hand, the agitation apparatus of the third embodiment uses a holder of the reaction vessel as the positioning member, and adjusts and determines the relative arrangement of the power transmitter and the power receiver by detaching and attaching the reaction vessel from and to the holder. FIG. 28 shows the agitation apparatus and the vessel according to the third embodiment of the present invention, and is a perspective view of the vessel according to the third embodiment and a block diagram of the configuration of the agitation apparatus.

An agitation apparatus 45 includes a power transmission element 46 as a power transmitter, a holder 47, and a surface-acoustic-wave element 48, as shown in FIG. 28. The agitation apparatus 45 is placed on a table, for example, and is employed to agitate each of the liquid sample retained in the reaction vessel 5.

The power transmission element 46 includes an RF transmission antenna 46a, a driving circuit 46b, and a controller 46c, that configured similarly to those in the power transmission element 31. The RF transmission antenna 46a is arranged on a side wall 47b of the holder 47.

The holder 47 is a positioning member which has an insertion portion 47a to which the reaction vessel 5 is detachably attached, formed in a rectangular-tube-like shape as shown in FIG. 28, and employed at the time of agitation of the liquid sample in the reaction vessel 5. When the reaction vessel 5 is inserted and attached to the insertion portion 47a, the holder 47 adjusts and determines the relative arrangement of the RF transmission antenna 46a and an antenna 48c.

The surface-acoustic-wave element 48 has the same configuration as that of the surface-acoustic-wave element 33, and a sound wave generator 48b including the interdigital transducers (IDT) is arranged integrally with the antenna 48c on a surface of a substrate 48a. The surface-acoustic-wave element 48 is attached to the side wall 5c of the reaction vessel 5 with the acoustic matching layer (not shown) of epoxy resin or the like posed therebetween with the sound wave generator 48b and the antenna 48c facing outward. The surface-acoustic-wave element 48 is attached onto the side wall 5c so that the surface-acoustic-wave element 48 is within the operable range of the RF transmission antenna 46a when the reaction vessel 5 is inserted and attached to the insertion portion 47a of the holder 47. The surface-acoustic-wave element 48 is attached to the reaction vessel 5 so that plural interdigital transducers of the sound wave generator 48b are arranged in a vertical direction and the antenna 48c is arranged at a portion other than the portion where the photometric window 5b is arranged on the same side surface as that on which the photometric window 5b is provided, as shown in FIG. 28. The surface-acoustic-wave element 48 receives the electric waves sent from the power transmission element 46 with the antenna 48c, to generate the surface acoustic waves (ultrasound waves) in the sound wave generator 48b according to the electromotive force generated by the resonance.

In the agitation apparatus 45 having the above-described configuration, when the reaction vessel 5 is inserted and attached to the insertion portion 47a of the holder 47, the RF transmission antenna 46a and the antenna 48c come to oppose with each other, and the electric waves sent from the RF transmission antenna 46a is received by the antenna 48c of the surface-acoustic-wave element 48. Then, in the surface-acoustic-wave element 48, electromotive force is generated by the resonance, the surface acoustic waves (ultrasound waves) are generated in the sound wave generator 48b, and the surface acoustic waves propagate through the acoustic matching layer and the side wall 5c into the reaction vessel 5, and leak out into the liquid sample having close acoustic impedance. As a result, counterclockwise flow and the clockwise flow Fcc are generated in the liquid sample in the reaction vessel 5 originating from a position corresponding to the sound wave generator 48b, similarly to the flows generated in the agitation apparatus 30, and the dispensed reagent and specimen are agitated.

As described above, the agitation apparatus 45 has the same advantages as those of the agitation apparatus 30, and in addition, the agitation apparatus 45 adjusts and determines the relative arrangement of the RF transmission antenna 46a and the antenna 48c using the holder 47. When the surface-acoustic-wave element 48 is arranged on the bottom surface of the reaction vessel 5, the RF transmission antenna 46a may be arranged on the bottom surface of the holder 47, and the relative arrangement of the RF transmission antenna 46a and the antenna 48c may be adjusted by the holder 47 when the reaction vessel 5 is inserted and attached to the holder 47. Here, the agitation apparatus 45 transmits the power in a non-contact manner from the power transmission element 46 to the surface-acoustic-wave element 48 attached to the reaction vessel 5 using the RF transmission antenna 46a and the antenna 48c. Therefore, the agitation apparatus 45, similarly to the agitation apparatus 20 of the first embodiment, realizes excellent energy transmission efficiency, and simple maintenance work; and further, the surface-acoustic-wave element 48 has more simplified and downsized configuration compared with that in the agitation apparatus 20, whereby the agitation apparatus itself can be further downsized.

The reaction vessel in the analysis apparatus, in particular, the automatic analysis apparatus that analyzes living specimen such as blood is required to be formed in an extremely small size of a capacity of a few μL to a few tens μL in order to downsize the apparatus and to alleviate the pains of a subject by minimizing the required amount of living specimen. When the capacity of the reaction vessel 5 is extremely small, an opening area of the vessel decreases accordingly. When the capacity is extremely small, an influence of a surface tension in the reaction vessel increases to obstruct injection and discharge of the liquid such as specimen, reagent, and cleaning liquid.

Figure 29:
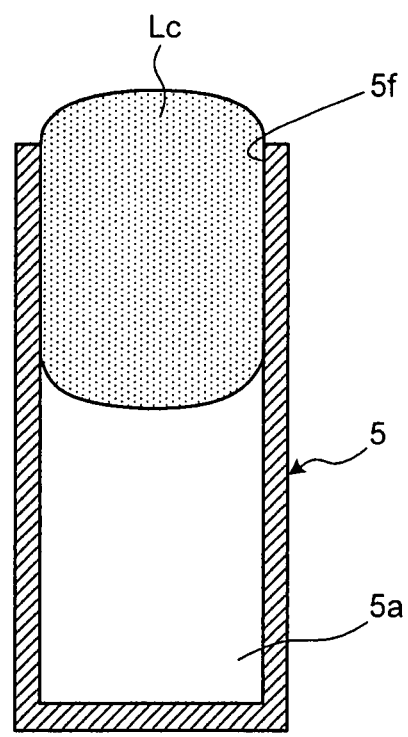
FIG. 29 is a sectional view of a miniaturization of the vessel of FIG. 28, where an upper opening is clogged with a dribbled cleaning liquid.

For example, if the reaction vessel 5 has an extremely small capacity, an upper opening 5f which serves as an inlet and an outlet of the cleaning liquid is also narrow. Therefore, when the washing mechanism 13 injects the cleaning liquid into the reaction vessel 5 to wash the reaction vessel 5, the nozzle 13a of the washing mechanism 13 cannot pass through the opening 5f. Hence, the washing mechanism 13 delivers the cleaning liquid through the nozzle 13a from above the opening 5f of the reaction vessel 5 by drops. However, the entrance of the cleaning liquid into the retaining portion 5a is obstructed by the surface tension in the reaction vessel 5, and the cleaning liquid Lc clogs the opening 5f above the retaining portion 5a as shown in FIG. 29.

Figure 30:
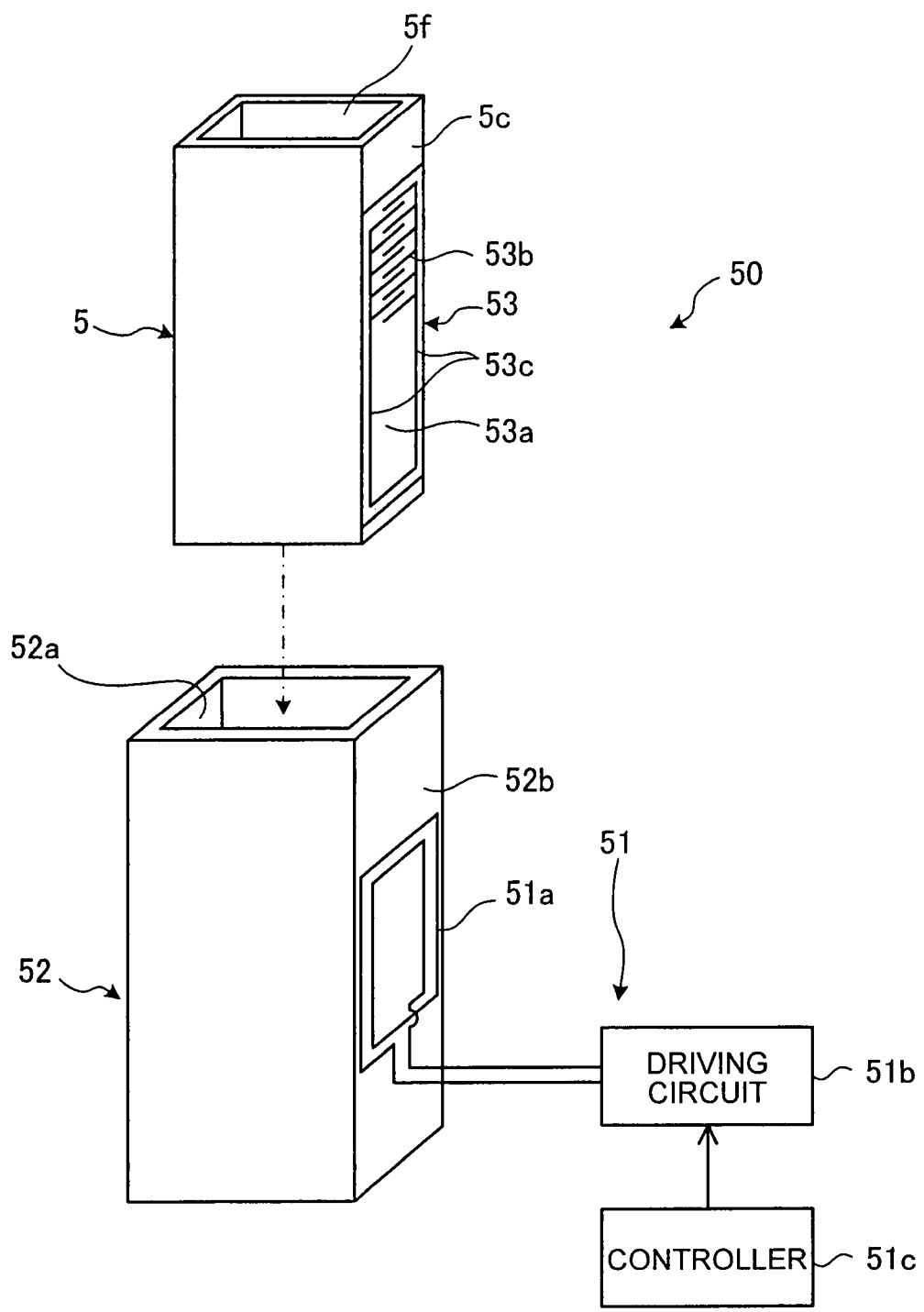
FIG. 30 shows an agitation apparatus which employs the surface-acoustic-wave element as an agitator that agitates a liquid and as an introducing unit that introduces the liquid into a retaining portion of the vessel.

To alleviate the above inconveniences, the agitation apparatus of the present invention uses the surface-acoustic-wave element that agitates the liquid by sound waves as an introducing unit that introduces the liquid such as cleaning liquid, specimen, and reagent into the retaining portion 5a of the reaction vessel 5, as a transfer unit that transfers the liquid from the retaining portion 5a to the opening 5f which serves as an outlet, as a discharge unit that discharges the liquid from the reaction vessel 5, and as a dryer that dries out the liquid, for example. Specifically, as in an agitation apparatus 50 shown in FIG. 30, a surface-acoustic-wave element 53 which serves also as the introducing unit is attached to the side wall 5c in such a manner that a sound wave generator 53b is arranged at the upper side of the reaction vessel 5. An RF transmission antenna 51a is arranged on a side wall 52b of a holder 52. The RF transmission antenna 51a is formed in a corresponding size at a corresponding position to the size and the position of an antenna 53c of the surface-acoustic-wave element 53. Since the discharge of the liquid such as cleaning liquid from the reaction vessel 5, to which the surface-acoustic-wave element 53 is attached, is difficult, the reaction vessel 5 is used as a disposable element. Though a substrate 53a of the surface-acoustic-wave element 53 is attached to the side wall 5c with the acoustic matching layer posed therebetween, the acoustic matching layer is not particularly shown in the drawings referred to in the following description.

Figure 31:
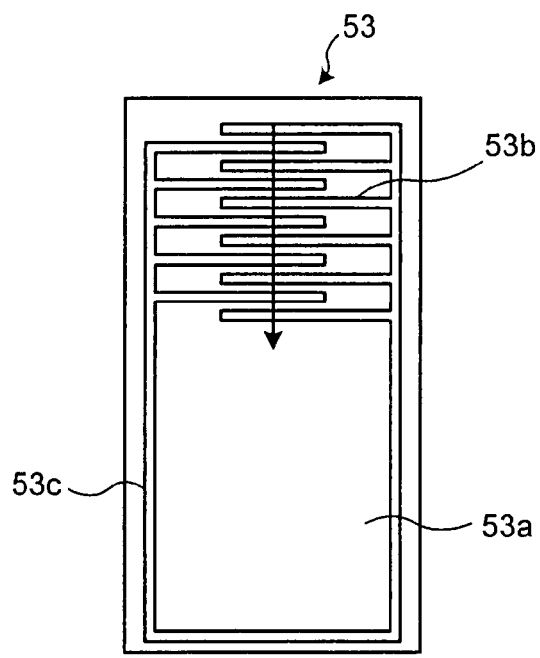
FIG. 31 is a front elevational view of the surface-acoustic-wave element employed in the vessel of FIG. 30.

In the agitation apparatus 50 having the above configuration, if the cleaning liquid Lc injected by the washing mechanism 13 to wash the reaction vessel 5 clogs the opening 5f, the agitation apparatus 50 sends the power from the RF transmission antenna 51a of the power transmission element 51 to the antenna 53c under the control of a controller 51c in a non-contact manner while maintaining the reaction vessel 5 inserted in an insertion portion 52a of the holder 52. Then, in the surface-acoustic-wave element 53, the sound wave generator 53b, which is arranged at the upper portion of the reaction vessel 5, emits the sound waves downward as shown by an arrow in FIG. 31.

Figure 32:
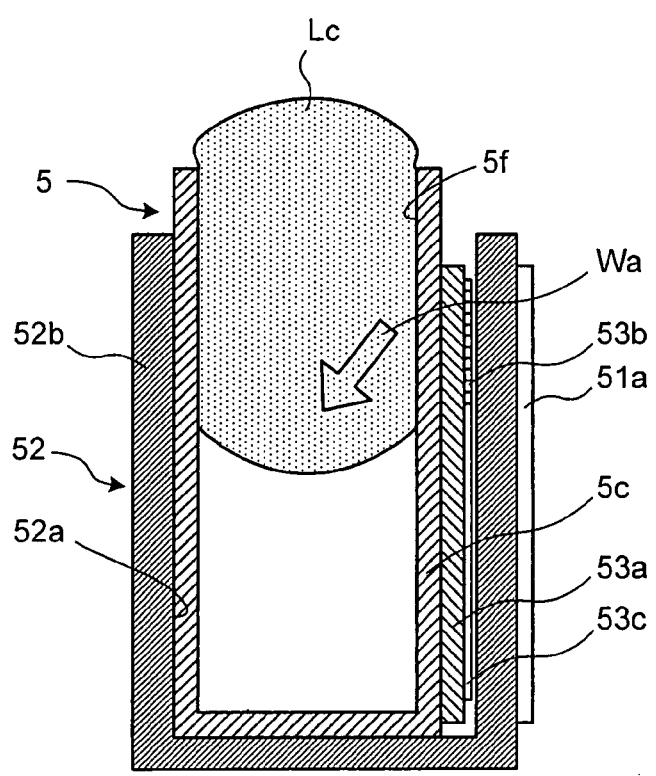
FIG. 32 is a sectional view of the vessel and a holder of FIG. 30.
Figure 33:
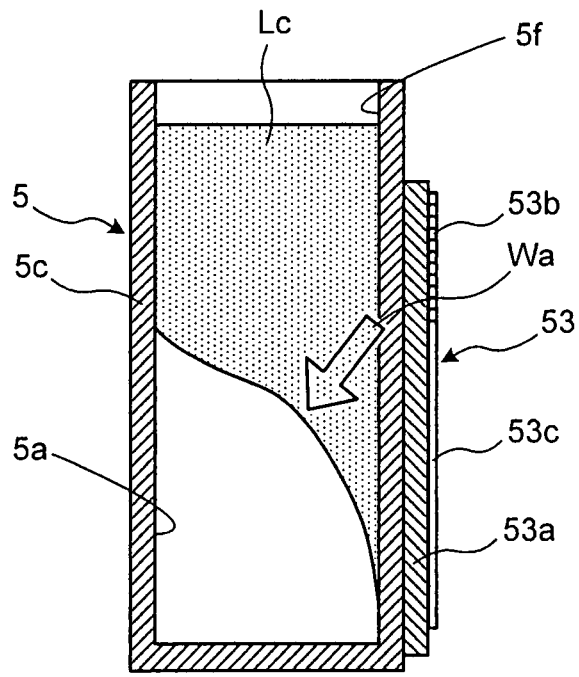
FIG. 33 is a sectional view showing how the surface-acoustic-wave element introduces the cleaning liquid into the vessel of FIG. 30.

Therefore, sound waves Wa generated by the sound wave generator 53b leak out from the inner wall surface to the cleaning liquid Lc in a diagonally downward direction as shown in FIG. 32. The leaking sound waves Wa generates a sound flow directing diagonally downward in the cleaning liquid Lc. In the agitation apparatus 50, the controller 51c makes the voltage applied to the sound wave generator 53b, i.e., strength of driving energy of the sound wave generator 53b, larger than the surface tension of the cleaning liquid Lc. Then, the sound flow generated by the sound waves Wa pushes a lower part of the cleaning liquid Lc that clogs the opening 5f downward as shown in FIG. 33, and eventually the whole of the cleaning liquid Lc is drawn into the retaining portion 5a.

Figure 34:
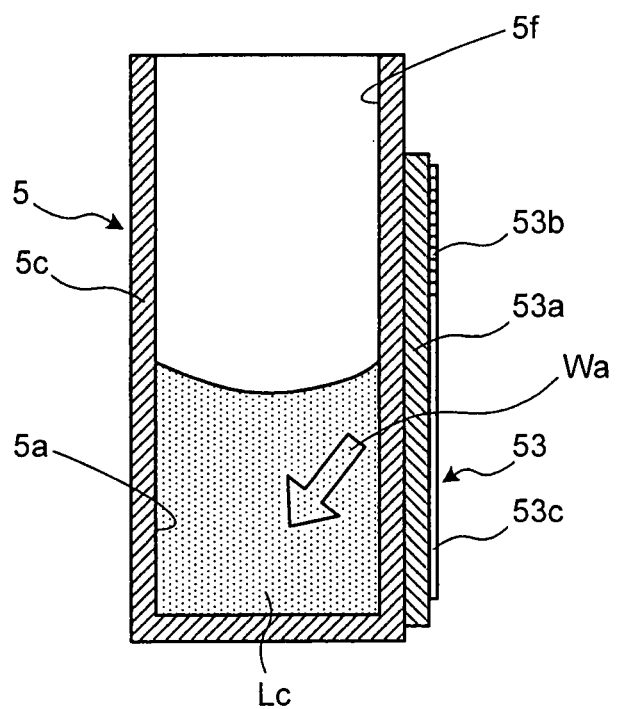
FIG. 34 is a sectional view showing a state after the surface-acoustic-wave element introduces the cleaning liquid into the vessel of FIG. 30.

As a result, the cleaning liquid Lc that clogs the opening 5f is eventually shifted downward entirely and introduced into the retaining portion 5a as shown in FIG. 34. Thus, the interior of the reaction vessel 5 is washed by the cleaning liquid Lc that moves from the opening 5f downward. Here, the sound wave generator 53b also emits the sound waves upward, where there is no substrate 53a but only the air. The sound waves emitted upward from the sound wave generator 53b does not propagate through the air due to difference in acoustic impedance, and only the sound waves emitted downward leak out to the cleaning liquid Lc.

Figure 35:
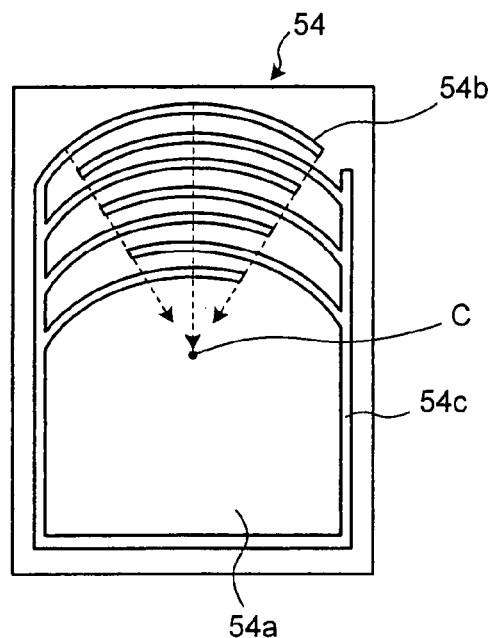
FIG. 35 is a front elevational view of another example of the surface-acoustic-wave element employed in the vessel of FIG. 30.

When the agitation apparatus 50 employs a surface-acoustic-wave element 54 shown in FIG. 35 as the surface-acoustic-wave element serving also as the introducing unit, the transfer efficiency of the liquid can be increased. Specifically, the surface-acoustic-wave element 54 includes interdigital transducers (IDT) that constitute a sound wave generator 54b arranged on a substrate 54a in a concentric manner so that a center C (focusing point) is vertically downward, and an antenna 54c. Thus, in the surface-acoustic-wave element 54, the sound waves emitted from the sound wave generator 54b converge on the center C of the interdigital transducers below the sound wave generator 54b. Accordingly, the sound flow generated in the cleaning liquid converges on a point corresponding to the center C of the interdigital transducers, which realizes efficient downward transfer of the cleaning liquid that clogs the opening 5f.

On the other hand, since the surface-acoustic-wave element can transfer the liquid such as cleaning liquid, specimen, and reagent, the surface-acoustic-wave element can be used also as the transfer unit that transfers the liquid to the outlet of the reaction vessel or as the discharge unit that discharges the liquid from the reaction vessel. When the surface-acoustic-wave element is used as described above, however, different surface-acoustic-wave elements need to be provided separately as a surface-acoustic-wave element used also as a liquid introducing unit, and as a surface-acoustic-wave element used also as the transfer unit or the discharge unit. Hence, the agitation apparatus uses a reaction vessel 55 and a holder 57 shown in FIG. 36 in place of the reaction vessel 5 and the holder 52 shown in FIG. 30. The reaction vessel 55 has a surface-acoustic-wave element which is used also as the liquid introducing unit, and a surface-acoustic-wave element which is used also as the transfer unit and the discharge unit, and is able to easily transfer the liquid such as cleaning liquid to the outlet and discharge. In this case, the reaction vessel 55 is not used as a disposable element and reused.

Figure 36:
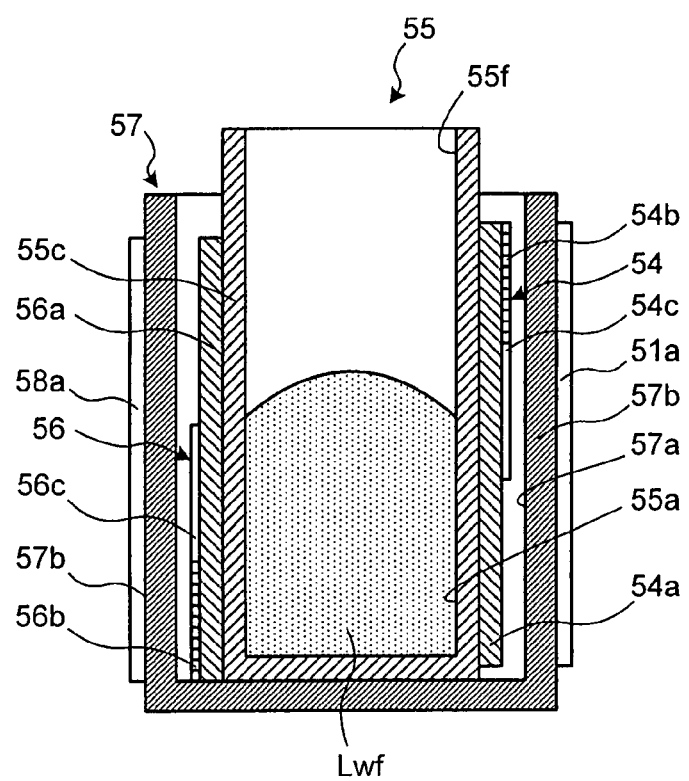
FIG. 36 is a front elevational view of a modified example of the vessel and the holder.

As shown in FIG. 36, in the reaction vessel 55, a surface-acoustic-wave element 56, which transfers the liquid to an opening 55f, i.e., an outlet, is attached to a side wall 55c opposing to a side wall 55c on which the surface-acoustic-wave element 54 is attached. The surface-acoustic-wave element 56 serves both as the transfer unit that transfers the liquid introduced into a retaining portion 55a to the opening 55f and the discharge unit that discharges the liquid to the outside, and includes a sound wave generator 56b which has the same configuration as that of the sound wave generator 54b and arranged at a lower portion of the reaction vessel 55, and a substrate 56a attached to the side wall 55c. On the other hand, the holder 57 includes an RF transmission antenna 58a attached onto a side wall 57b opposing to a side wall 57b on which the RF transmission antenna 51a is arranged. The RF transmission antenna 58a sends the power transmitted from a power transmission element 58 which is different from the power transmission element 51 to an antenna 56c for the liquid discharge under the control of a controller 58c.

When the cleaning liquid Lc injected by the washing mechanism 13 for washing the reaction vessel 55 clogs the opening 55f, the agitation apparatus including the reaction vessel 55 and the holder 57 sends the power from the RF transmission antenna 51a of the power transmission element 51 to the antenna 54c in a non-contact manner under the control of the controller 51c while keeping the reaction vessel 55 inserted in an insertion portion 57a of the holder 57. Then, the sound flow generated by the sound waves emitted from the sound wave generator 54b causes the cleaning liquid to be introduced into the retaining portion 55a while washing up the interior of the reaction vessel 55. As shown in FIG. 36, the waste fluid Lwf of the cleaning liquid is transferred to the lower portion of the retaining portion 55a. Depending on the type of the liquid sample retained in the retaining portion 55a, the agitation apparatus may continue to drive the sound wave generator 54b for a while after the waste fluid Lwf of the cleaning liquid moves to the lower portion of the retaining portion 55a so as to keep washing the interior of the reaction vessel 55.

Figure 37:
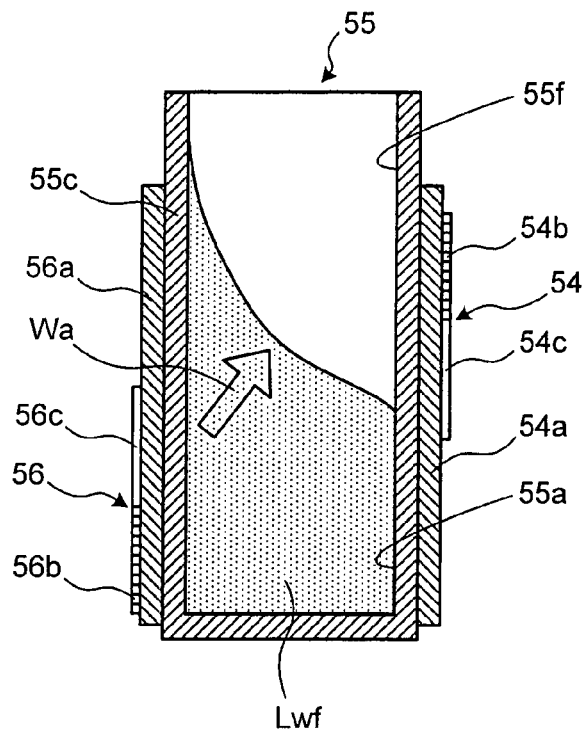
FIG. 37 is a sectional view showing how waste fluid of the cleaning liquid is discharged from the vessel of FIG. 36.

After transferring the waste fluid Lwf of the cleaning liquid to the lower portion of the retaining portion 55a, the agitation apparatus sends the power from the RF transmission antenna 58a of the power transmission element 58 to the antenna 56c in a non-contact manner under the control of the controller 58c. Since the sound wave generator 56b of the surface-acoustic-wave element 56 is arranged at the lower portion of the reaction vessel 55, the sound waves Wa generated from the sound wave generator 56b leak out from the inner wall surface of the reaction vessel 55 to the waste fluid Lwf of the cleaning liquid in a diagonally upward direction as shown in FIG. 37. The sound waves Wa leaking out in the diagonally upward direction causes the sound flow directing diagonally upward in the waste fluid Lwf of the cleaning liquid retained in the lower portion of the retaining portion 55a.

Figure 38:
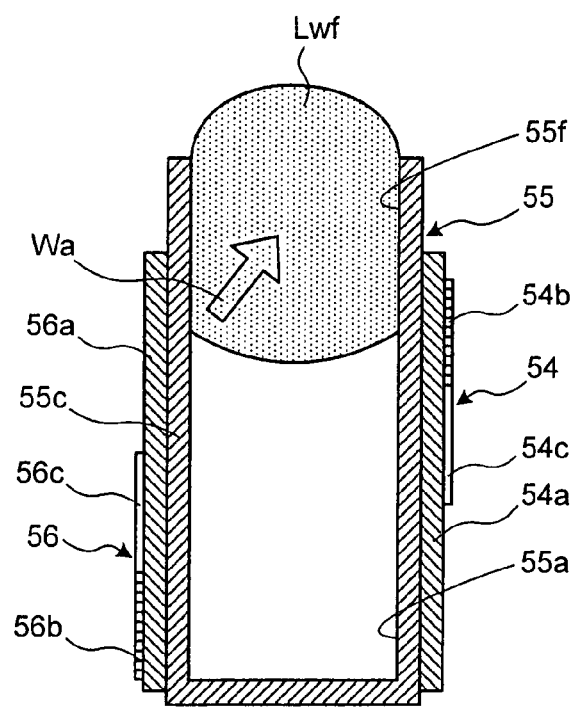
FIG. 38 is a sectional view of the vessel of FIG. 36 in which whole of the waste fluid of the cleaning liquid is moved upward to clog the opening.

The agitation apparatus makes the voltage applied to the sound wave generator 56b, i.e., the driving energy strength of the sound wave generator 56b higher than the surface tension of the cleaning liquid Lc using the controller 58c. Then, a portion of the waste fluid Lwf of the cleaning liquid located at the side of the surface-acoustic-wave element 56 moves upward due to the sound flow generated by the sound waves Wa as shown in FIG. 37, and eventually the whole of the waste fluid Lwf of the cleaning liquid moves upward. As a result, the waste fluid Lwf of the cleaning liquid retained in the lower portion of the retaining portion 55a is eventually transferred to the upper opening 55f as shown in FIG. 38. The waste fluid Lwf of the cleaning liquid clogs the opening 55f which serves as the outlet in the reaction vessel 55.

Figure 39:
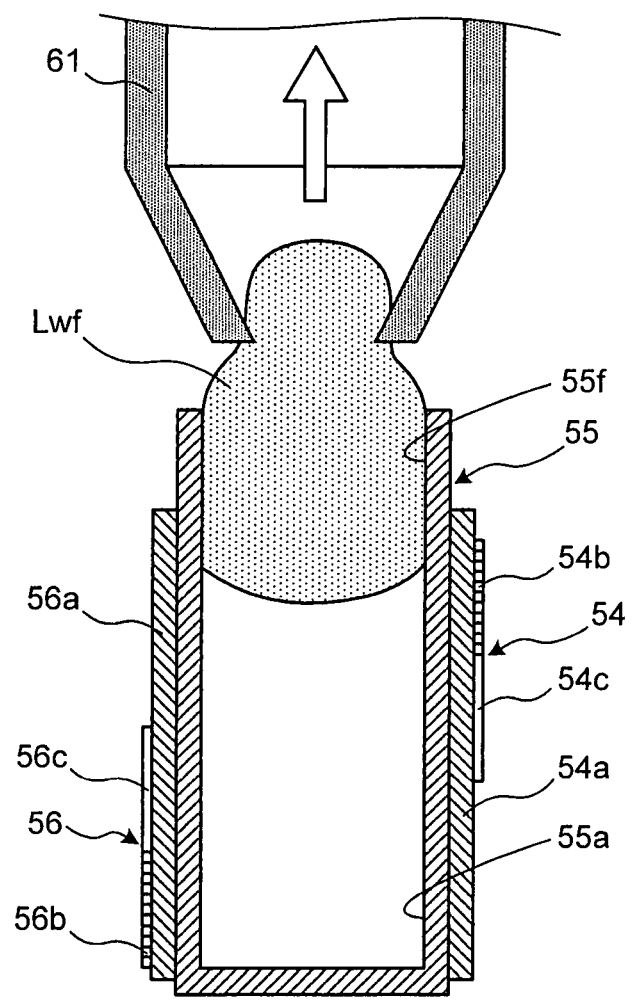
FIG. 39 is a sectional view showing how the waste fluid of the cleaning liquid is sucked through a suction nozzle from the vessel of FIG. 38.

The waste fluid Lwf of the cleaning liquid clogging the opening 55f of the reaction vessel 55 is sucked by a suction nozzle 61 from above as shown in FIG. 39. The area of the opening 55f of the reaction vessel 55 is extremely small since the capacity of the reaction vessel 55 is made extremely small. However, since the suction nozzle 61 is employed simply to suck the waste fluid Lwf of the cleaning liquid from above and is not inserted into the reaction vessel 55 from the opening 55f, the conventional suction nozzle can be used.

Figure 40:
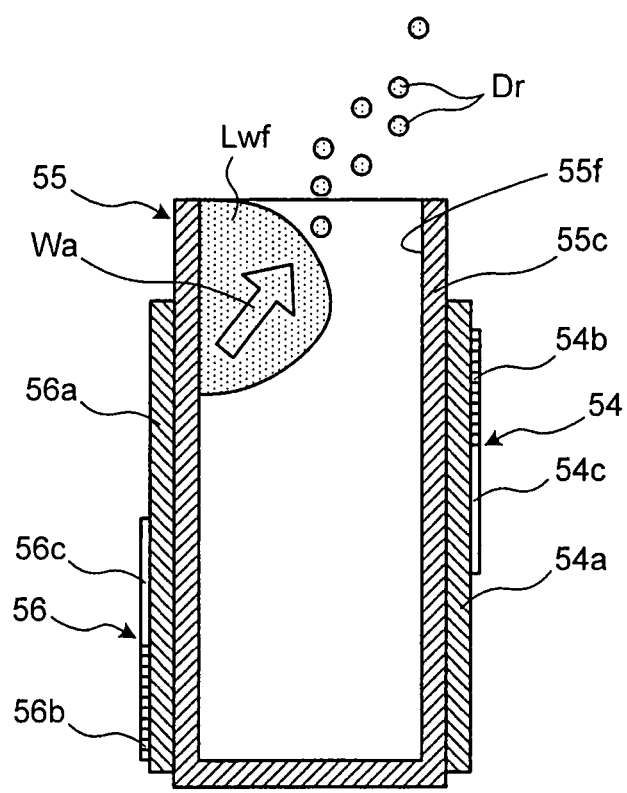
FIG. 40 is a sectional view showing how the remaining waste fluid of the cleaning liquid is blown away from the vessel of FIG. 38 in droplet forms.

After the waste fluid Lwf of the cleaning liquid is sucked out, the sound wave generator 56b is driven by a higher power under the control of the controller 58c. The sound wave generator 56b is configured with concentric interdigital transducers (IDT) similarly to the sound wave generator 54b. Therefore, the high-power sound waves converge on a center C of the circular arc of the sound wave generator 56b. Even if a portion of the waste fluid Lwf of the cleaning liquid remains after the suction, it is blown by the converged sound waves. Thus, the waste fluid Lwf of the cleaning liquid in the reaction vessel 55 is completely discharged. If the sound wave generator 56b is continuously driven, the waste fluid Lwf of the cleaning liquid is blown in a spray-like form, whereas if the sound wave generator 56b is pulse-driven, the waste fluid Lwf of the cleaning liquid is blown in a droplet (Dr) form as shown in FIG. 40. After the discharge of the waste fluid Lwf of the cleaning liquid in the above-described manner, the reaction table 4 transfers the reaction vessel 55 for the next analysis of the specimen.

Figure 41:
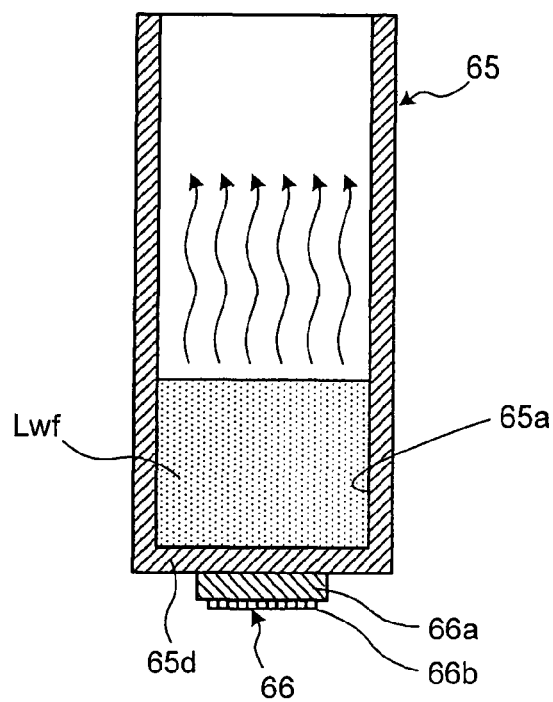
FIG. 41 is a sectional view of another vessel which includes the surface-acoustic-wave element attached on the bottom wall and evaporates the waste fluid of the cleaning liquid to discharge.
Figure 42:
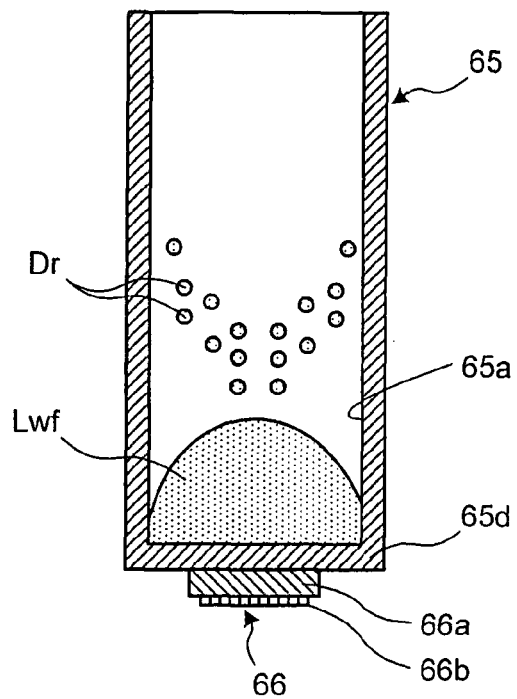
FIG. 42 is a sectional view showing how the remaining waste fluid of the cleaning liquid is blown away from the vessel of FIG. 41 in droplet forms.

In the reaction vessel including the surface-acoustic-wave elements for liquid introduction and liquid discharge, a surface-acoustic-wave element 66 may be attached to the lower surface of a bottom wall 65d for discharging as in a reaction vessel 65 shown in FIG. 41. A sound wave generator 66b discharges the liquid by supplying an excessive power, thereby, for example, heating up the waste fluid Lwf of the cleaning liquid remaining in the lower portion of a retaining portion 65a, evaporating, and drying the waste fluid Lwf of the cleaning liquid. Alternatively, the sound wave generator 66b of the reaction vessel 65 may be pulse-driven so as to discharge the waste fluid Lwf of the cleaning liquid remaining in the lower portion of the retaining portion 65a by blowing in a droplet (Dr) form as shown in FIG. 42.

Fourth Embodiment

Figure 43:
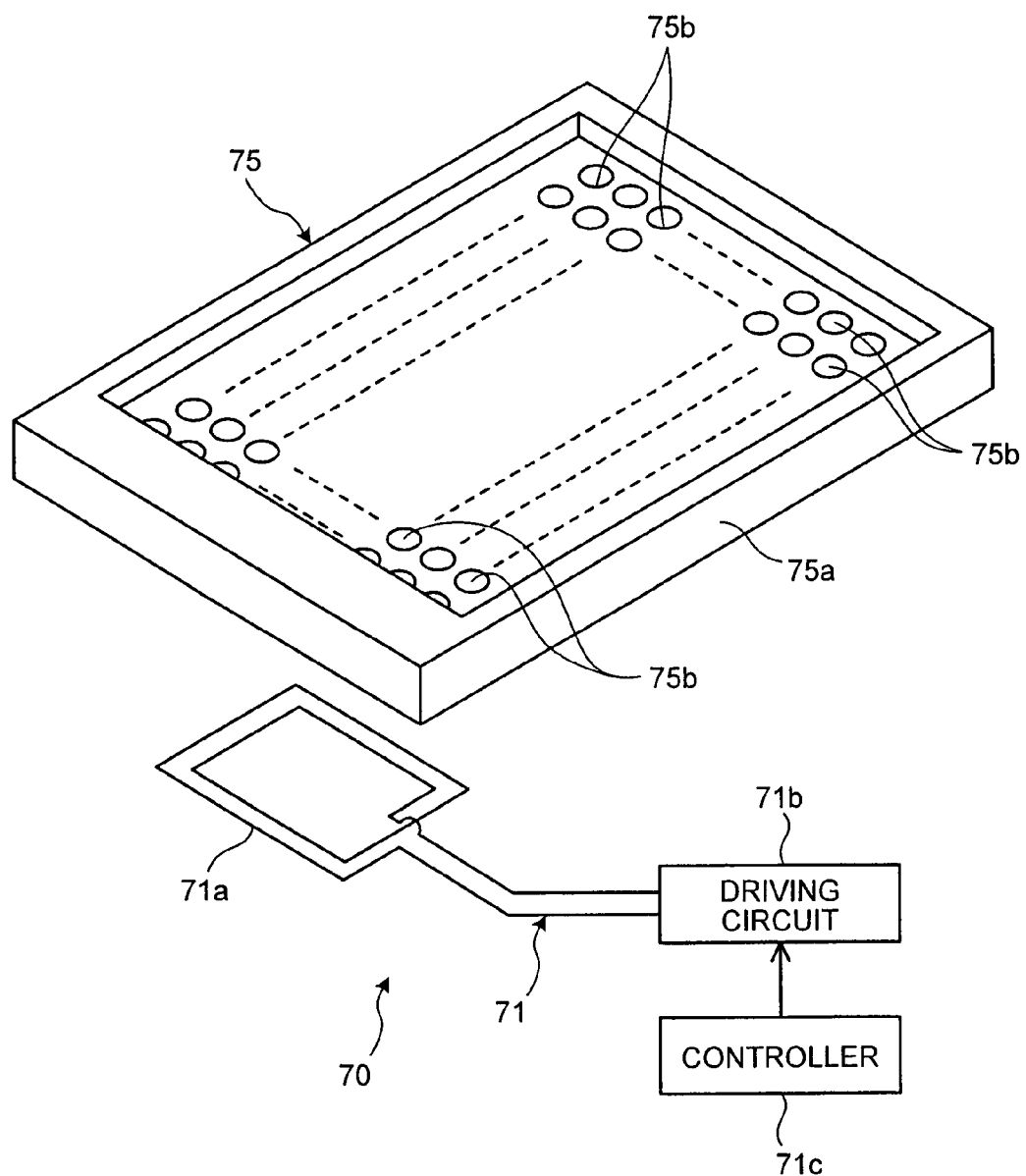
FIG. 43 shows a fourth embodiment of the present invention and is a perspective view of a microplate having plural retaining portions for retaining the liquid and an agitation apparatus.
Figure 44:
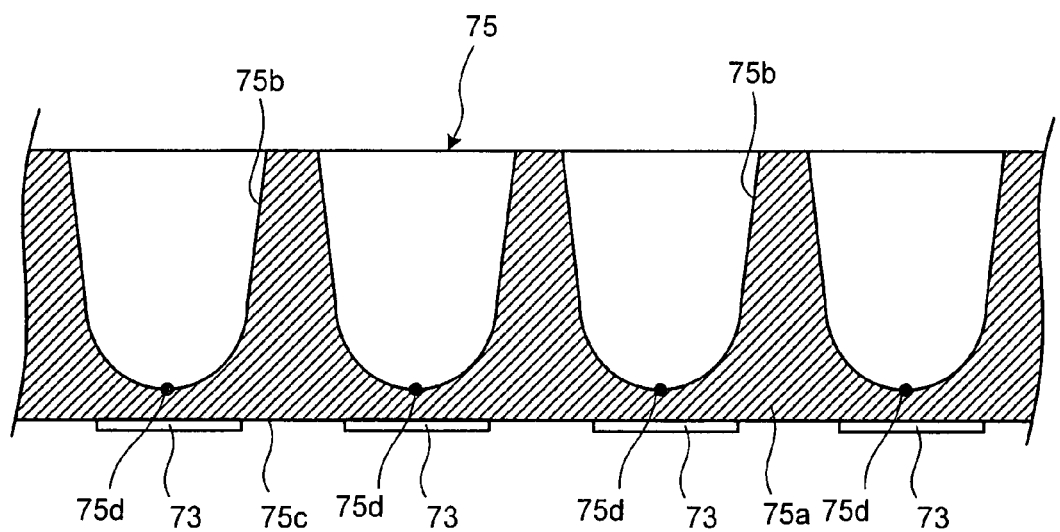
FIG. 44 is a partial sectional view of the microplate of FIG. 43 with the surface-acoustic-wave elements.
Figure 45:
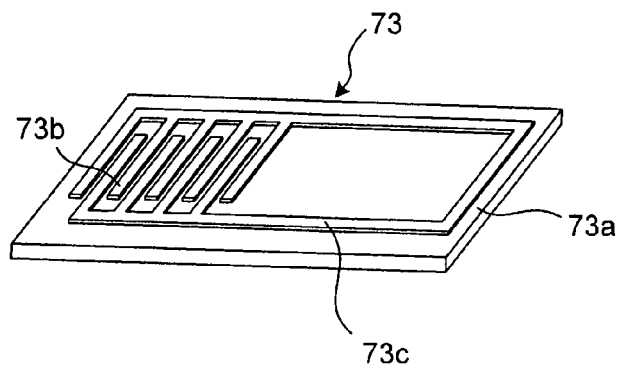
FIG. 45 is an enlarged perspective view of the surface-acoustic-wave element of FIG. 44.

An agitation apparatus and a vessel according to a fourth embodiment of the present invention will be described in detail below with reference to the accompanying drawings. The first and the second embodiments are the vessel having one liquid retaining portion and the agitation apparatus therefor, whereas, the fourth embodiment is a vessel having plural liquid retaining portions and an agitation apparatus therefor. FIG. 43 is a perspective view of a microplate having plural retaining portions to retain the liquid and an agitation apparatus. FIG. 44 is a partial sectional view of the microplate of FIG. 43 and the surface-acoustic-wave elements. FIG. 45 is an enlarged perspective view of the surface-acoustic-wave element shown in FIG. 44.

An agitation apparatus 70 includes a power transmission element 71 arranged below a microplate 75, and a surface-acoustic-wave element 73 which is arranged on a bottom surface of the microplate 75 below a well 75b, as shown in FIGS. 43 and 44, and agitates the liquid sample retained in the plural wells 75b.

The microplate 75 includes, as shown in FIGS. 43 and 44, a main body 75a formed in a rectangular shape, and the plural wells 75b arranged like a matrix on an upper surface of the main body 75a and serving as retaining portions of the liquid sample. The microplate 75 is a reaction vessel employed to receive dispensed reagent and specimen such as blood and bodily fluid in each well 75b to induce reaction and to optically measure the reaction liquid to analyze the component, concentration, or the like of the specimen.

The power transmission element 71 is supported by a positioning member (not shown) which controls a distance from the microplate 75 and a two-dimensional position along a plate surface of the microplate 75, and includes an RF transmission antenna 71a which is arranged opposite to the plural surface-acoustic-wave elements 73, a driving circuit 71b, and a controller 71c as shown in FIG. 43. The power transmission element 71 transmits the power supplied from an alternate-current power supply as electric waves to the surface-acoustic-wave element 73 via the RF transmission antenna 71a while moving in the two-dimensional direction along the plate surface of the microplate 75. The relative arrangement of the power transmission element 71 is adjusted and determined by the positioning member so that the RF transmission antenna 71a and an antenna 73c described later of the surface-acoustic-wave element 73 are opposed to each other at the time of power transmission to the surface-acoustic-wave element 73.

The surface-acoustic-wave element 73 is attached to a bottom surface 75c below each well 75b with an acoustic matching layer (not shown) of epoxy resin or the like posed therebetween. As shown in FIG. 45, a sound wave generator 73b including the interdigital transducers (IDT) and the antenna 73c serving as a power receiver are formed integrally on the surface of a substrate 73a. The surface-acoustic-wave element 73 is positioned so that the center of the sound wave generator 73b is aligned with a vertex 75d of the well 75b, and attached to the bottom surface 75c of the microplate 75. One surface-acoustic-wave element 73 may be attached to each well 75b as shown in FIG. 44, or one surface-acoustic-wave element 73 may be attached so as to cover a unit of plural wells 75b. The surface-acoustic-wave element 73 receives the electric waves transmitted from the power transmission element 71 by the antenna 73c to generate the surface acoustic waves (ultrasound waves) in the sound wave generator 73b according to the electromotive force generated by the resonance.

In the agitation apparatus 70 having the above-described configuration, the power transmission element 71 transmits the electric waves from the RF transmission antenna 71a under the control of the controller 71c when the RF transmission antenna 71a and the antenna 73c oppose with each other. The antenna 73c of the surface-acoustic-wave element 73 placed opposite to the power transmission element 71 receives the electric waves, and the electromotive force is generated by the resonance. In the agitation apparatus 70, the surface acoustic waves (ultrasound waves) are generated in the sound wave generator 73b due to the electromotive force, and the surface acoustic waves propagate through the acoustic matching layer to the inside of the main body 75a of the microplate 75, and then leak out to the liquid sample having close acoustic impedance. As a result, in the microplate 75, the flows are generated in the liquid sample, and the reagent and the specimen dispensed in each well 75b are agitated.

After the agitation and the reaction of the reagent and the specimen, an imager such as a CCD camera picks up an image of the liquid sample from above the microplate 75, and the components of the specimen are analyzed based on obtained imaged data.

As described above, the agitation apparatus 70 transmits the power in a non-contact manner from the power transmission element 71 to the surface-acoustic-wave element 73 attached to the microplate 75 using the RF transmission antenna 71a and the antenna 73c, and agitates the reagent and the specimen dispensed into the plural wells 75b. Therefore, the agitation apparatus 70 realizes excellent energy transmission efficiency and simple maintenance work similarly to the agitation apparatus 30; and further, the surface-acoustic-wave element 73 has more simplified and small configuration compared with that in the agitation apparatus 20 of the first embodiment, whereby the automatic analysis apparatus can be further downsized.

INDUSTRIAL APPLICABILITY

As can be seen from the foregoing, an agitation apparatus, a vessel, and an analysis apparatus including the agitation apparatus according to the present invention have excellent energy transmission efficiency, simplified configuration which allows for downsizing, and are useful for realizing simplified maintenance works, and in particular are suitable for being used in an automatic analysis apparatus.

The invention claimed is:

1. An agitation apparatus which agitates a liquid retained in a vessel using sound waves, comprising:
   a vessel for retaining the liquid;
   a power transmitter that transmits power;
   a power receiver which receives the power transmitted from the power transmitter and whose relative arrangement with respect to the power transmitter is changeable;
   a control unit;
   a positioning member controlled by the control unit, and configured to change a position of at least one of the power transmitter and the power receiver; and
   a sound wave generator that generates sound waves to agitate the liquid by converting the power received by the power receiver.

2. The agitation apparatus according to claim 1, wherein the control unit determines and instructs the positioning member to adjust the relative arrangement of the power transmitter and the power receiver.

3. The agitation apparatus according to claim 2, wherein the control unit instructs the positioning member to adjust the relative arrangement so that a distance between the power transmitter and the power receiver is different in a power-transmission time and non-power-transmission time.

4. The agitation apparatus according to claim 3, wherein the control unit instructs the positioning member to adjust so that the distance between the power transmitter and the power receiver is longer in the non-power-transmission time than in the power-transmission time.

5. The agitation apparatus according to claim 3, wherein the control unit instructs the positioning member to bring the power transmitter and the power receiver into contact with each other or close to each other at the power-transmission time.

6. The agitation apparatus according to claim 1, wherein the power receiver is arranged on a different member from a member on which the power transmitter is arranged.

7. The agitation apparatus according to claim 1, wherein the sound wave generator and the power receiver are substantially fixed to the vessel, and the positioning member is configured to move the power transmitter relative to the vessel.

8. The agitation apparatus according to claim 7, wherein the sound wave generator is arranged on a side surface of the vessel.

9. The agitation apparatus according to claim 8, wherein the power transmitter is arranged horizontally opposing to the sound wave generator.

10. The agitation apparatus according to claim 7, wherein the sound wave generator is arranged on a bottom surface of the vessel.

11. The agitation apparatus according to claim 10, wherein the power transmitter is arranged vertically opposing to the sound wave generator.

12. The agitation apparatus according to claim 7, wherein the power transmitter and the power receiver are connected by a cable.

13. The agitation apparatus according to claim 7, wherein the power transmitter and the power receiver are connected by radio via antennas.

14. The agitation apparatus according to claim 13, wherein the power transmitter transmits power to the power receiver when an antenna on a power transmission side is placed opposite to an antenna of a power reception side of the power receiver.

15. The agitation apparatus according to claim 13, wherein the power receiver includes plural power receivers.

16. The agitation apparatus according to claim 1, wherein the vessel is formed of an optically transparent material and has one side surface, part of which is used as a photometric window.

17. The agitation apparatus according to claim 16, wherein the power receiver is arranged on a side surface on which the photometric window is provided, at a position where the photometric window is not arranged.

18. The agitation apparatus according to claim 16, wherein the power receiver is arranged on a surface which is different from the surface on which the photometric window is arranged.

19. The agitation apparatus according to claim 1, wherein the sound wave generator is an interdigital transducer of a surface-acoustic-wave element that generates surface acoustic waves according to an applied high-frequency alternate-current electric field.

20. The agitation apparatus according to claim 1, wherein the vessel includes plural vessels.

21. The agitation apparatus according to claim 1, wherein the vessel has plural retaining portions to retain the liquid.

22. An apparatus operable to analyze reaction liquid by agitating and causing a reaction of a liquid sample including a specimen and a reagent retained in a vessel, comprising an agitation apparatus which agitates a liquid retained in the vessel using sound waves, the agitation apparatus including:
   a vessel for retaining the liquid sample;
   a power transmitter that transmits power;
   a power receiver which receives the power transmitted from the power transmitter and whose relative arrangement with respect to the power transmitter is changeable;
   a control unit;
   a positioning member controlled by the control unit, and configured to change a position of at least one of the power transmitter and the power receiver; and
   a sound wave generator that generates sound waves to agitate the liquid by converting the power received by the power receiver.

* * * * *